US011484710B2

(12) United States Patent
Mantovani et al.

(10) Patent No.: US 11,484,710 B2
(45) Date of Patent: Nov. 1, 2022

(54) DEVICE AND SYSTEM FOR REAL-TIME GAIT MODULATION AND METHODS OF OPERATION THEREOF

(71) Applicant: Evolution Devices, Inc., Berkeley, CA (US)

(72) Inventors: Pierluigi Alfredo Mantovani, Berkeley, CA (US); Juan Manuel Rodriguez, Berkeley, CA (US); Petr Karashchuk, Seattle, WA (US); Andrew Ekelem, Fairfield, CA (US); Mohammed Aashyk Mohaiteen Hebsur Rahman, San Francisco, CA (US)

(73) Assignee: Evolution Devices, Inc., Berkeley, CA (US)

( * ) Notice: Subject to any disclaimer, the term of this patent is extended or adjusted under 35 U.S.C. 154(b) by 388 days.

(21) Appl. No.: 16/730,336

(22) Filed: Dec. 30, 2019

(65) Prior Publication Data
US 2020/0215324 A1    Jul. 9, 2020

Related U.S. Application Data

(60) Provisional application No. 62/789,133, filed on Jan. 7, 2019.

(51) Int. Cl.
*A61N 1/36*      (2006.01)
*A61N 1/04*      (2006.01)
(Continued)

(52) U.S. Cl.
CPC ........ *A61N 1/36003* (2013.01); *A61B 5/0022* (2013.01); *A61B 5/112* (2013.01);
(Continued)

(58) Field of Classification Search
CPC .............. A61N 1/36003; A61N 1/0452; A61N 1/0456; A61N 1/0476; A61N 1/3603;
(Continued)

(56) References Cited

U.S. PATENT DOCUMENTS

| 5,814,093 A | 9/1998 | Stein |
|---|---|---|
| 6,507,757 B1 | 1/2003 | Swain et al. |

(Continued)

*Primary Examiner* — Amanda K Hulbert
*Assistant Examiner* — Philip C Edwards
(74) *Attorney, Agent, or Firm* — Levine Bagade Han LLP

(57) ABSTRACT

Apparatus, systems, and methods for real-time gait modulation are disclosed. In one embodiment, a functional electrical stimulation (FES) device is disclosed comprising one or more elastic wearable articles, a control unit comprising a wireless communication module, one or more processors, one or more memory units, a portable power supply, an electrical muscle stimulation (EMS) generator, and an inertial measurement unit (IMU) comprising at least a gyroscope and an accelerometer. The FES device can also comprise one or more electrode arrays configured to be in physical contact with the limb of the user. The processors can be programmed to execute instructions to retrieve readings from the IMU, calculate a gait cycle percentage by inputting at least the IMU readings into a machine learning algorithm, and instruct the EMS generator to provide electrical stimulation via the one or more electrode arrays based in part on the gait cycle percentage calculated.

19 Claims, 11 Drawing Sheets

(51) Int. Cl.
    *A61B 5/11*     (2006.01)
    *A61B 5/00*     (2006.01)
    *G06F 3/01*     (2006.01)
    *G06N 3/08*     (2006.01)
    *G06N 20/00*     (2019.01)

(52) U.S. Cl.
    CPC .......... *A61B 5/6828* (2013.01); *A61N 1/0452* (2013.01); *A61N 1/0456* (2013.01); *A61N 1/0476* (2013.01); *A61N 1/3603* (2017.08); *G06F 3/011* (2013.01); *G06F 3/017* (2013.01); *G06N 3/08* (2013.01); *G06N 20/00* (2019.01); *A61B 2562/0219* (2013.01)

(58) Field of Classification Search
    CPC ..... A61B 5/0022; A61B 5/112; A61B 5/6828; G06N 20/00
    See application file for complete search history.

(56) References Cited

U.S. PATENT DOCUMENTS

| | | | |
|---|---|---|---|
| 8,209,022 | B2 | 6/2012 | Dar et al. |
| 8,788,049 | B2 | 7/2014 | Lasko et al. |
| 8,972,017 | B2 | 3/2015 | Dar et al. |
| 9,095,417 | B2 | 8/2015 | Dar et al. |
| 9,204,822 | B2 | 12/2015 | Lane et al. |
| 9,272,139 | B2 | 3/2016 | Hamilton et al. |
| 9,415,205 | B2 | 8/2016 | Lasko et al. |
| 9,867,985 | B2 | 1/2018 | Glukhovsky et al. |
| 10,016,598 | B2 | 7/2018 | Lasko et al. |
| 2012/0059432 | A1* | 3/2012 | Emborg ............ A61N 1/36034 607/49 |
| 2016/0107309 | A1* | 4/2016 | Walsh ................. A61B 5/6831 248/550 |
| 2018/0132757 | A1* | 5/2018 | Kong ................... A61B 5/6885 |
| 2018/0279915 | A1* | 10/2018 | Huang ................. A61B 5/1116 |

\* cited by examiner

MUSCLES OF HUMAN LEGS

DEVICE AND SYSTEM FOR REAL-TIME GAIT MODULATION AND METHODS OF OPERATION THEREOF

CROSS-REFERENCE TO RELATED APPLICATIONS

This application claims priority to U.S. Patent Application No. 62/789,133 filed Jan. 7, 2019, the content of which is incorporated herein by reference in its entirety.

TECHNICAL FIELD

This disclosure relates generally to the field of orthotics, more specifically, to improved devices, systems, and methods for real-time gait modulation.

BACKGROUND

Functional electrical stimulation (FES) is a treatment modality that applies electrical pulses to the neuromuscular system of a limb which has become paralyzed or weakened due to disease, injury, or aging. FES is commonly used as a treatment for patients exhibiting a condition known as drop foot. Patients suffering from drop foot often drag or lower their foot during the swing phase of the patient's gait cycle. To compensate for this dragging, a patient may swing their legs in a circular or exaggerated motion. This condition can lead to frequent falls and even short walks for such patients can be an exhaustive effort requiring excessive amounts of energy.

While orthotics and other gait modulation devices have been designed to treat gait-related impairments such as drop foot, such devices are often bulky and uncomfortable to wear. For example, certain such devices often comprise a rigid portion which can dig into the wearer's skin and is aesthetically displeasing. Moreover, other such devices require a heel sensor to be worn within the footwear of the user. This can lead to the user not being able to walk barefoot or in socks. This can also restrict the number of physical activities the user can undertake.

Furthermore, such devices often do not accurately calculate gait metrics based on real-time motion data. In addition, such devices often do not automatically generate stimuli based on real-time motion data. Moreover, some devices, such as those taught by U.S. Pat. No. 5,814,093, rely on a control method using tilt sensors. However, tilt parameters vary and require frequent tuning for appropriate stimulation timing. In addition, other devices, such as those taught by U.S. Pat. No. 6,507,757, rely on a control method whereby a footswitch coordinates stimulation timing by indicating foot-off and foot-strike. However, these types of devices rely on hardware being placed under the foot and are prone to false activation.

Therefore, improved devices, systems, and methods for real-time gait modulation are needed which address the challenges faced by current gait modulation devices. In addition, such a solution should provide added comfort, be easy to put on and take off by users, and provide data and metrics unavailable to users of current gait modulation devices. Moreover, such a solution should also not be overly complex and be cost-effective to manufacture.

SUMMARY

Improved devices, systems, and methods for real-time gait modulation are disclosed. In one embodiment, a functional electrical stimulation (FES) device comprises one or more elastic wearable articles configured to be worn on a limb of a user. The device can also comprise a control unit comprising a wireless communication module, one or more processors, one or more memory units, a portable power supply, an electrical muscle stimulation (EMS) generator, and an inertial measurement unit (IMU) comprising at least a gyroscope or accelerometer. A housing of the control unit can be coupled to at least one of the one or more elastic wearable articles. The device further comprises one or more electrode arrays configured to be in electrical communication with the EMS generator. In some embodiments, at least one of the one or more electrode arrays is configured to be coupled to an inner surface of at least one of the one or more elastic wearable articles. The electrodes of the electrode array(s) can be in physical contact with the limb of the user when the device is worn by the user.

The one or more processors of the device can be programmed to execute instructions stored in the one or more memory units to retrieve gyroscope readings and accelerometer readings from the IMU, calculate a gait cycle percentage by inputting the gyroscope readings and accelerometer readings into a machine learning algorithm, and instruct the EMS generator to provide electrical stimulation to the nerves and muscles of the limb via the one or more electrode arrays based in part on the gait cycle percentage calculated.

In some embodiments, the one or more elastic wearable articles can comprise a first elastic sleeve and a second elastic sleeve. The first elastic sleeve can be configured to be worn on a thigh of the user and the second elastic sleeve can be configured to be worn on a lower leg of the user between a knee and an ankle of the user. The one or more electrode arrays can comprise at least a first upper leg array, a second upper leg array, a first lower leg array, and a second lower leg array. The first upper leg array and the second upper leg array can be coupled to the inner surface of the first elastic sleeve. The first upper leg array and the second upper leg array can be in physical contact with a skin surface in proximity to a hamstring of the user when the first elastic sleeve is worn on the thigh of the user. Moreover, the first lower leg array and the second lower leg array can be coupled to the inner surface of the second elastic sleeve. The first lower leg array and the second lower leg array can be in physical contact with the skin surface in proximity to a tibialis anterior of the user when the second elastic sleeve is worn on the lower leg of the user.

Alternatively, the one or more elastic wearable articles can comprise one elastic sleeve or cuff configured to be worn on a lower leg of the user between a knee and an ankle of the user. The one or more electrode arrays can comprise at least one first lower leg array and a second lower leg array coupled to the inner surface of the elastic sleeve. The first lower leg array and the second lower leg array can be in physical contact with the skin surface in proximity to a tibialis anterior of the user when the elastic sleeve is worn on the lower leg of the user.

As previously mentioned, the IMU of the device can further comprise an accelerometer. The one or more processors can be programmed to execute instructions stored in the one or more memory units to retrieve accelerometer readings from the IMU, map gyroscope readings and accelerometer readings to three-dimensional angles of at least one of a hip, a knee, and a foot of the user throughout a gait cycle, and determine at least one of a foot strike pattern, a foot inclination angle at initial contact, a tibia angle at loading response, a hip extension during late stance, a trunk lean, a heel eversion, a foot progression angle, a pelvic drop, a knee flexion during stance, a stride length, a knee window, a vertical displacement of the center mass, and a heel whip of the user based in part on the gait cycle percentage calculated, the gyroscope readings, the accelerometer readings, and the mapped three-dimensional angles.

The wireless communication module can be configured to wirelessly transmit readings and walking metrics calculated from the IMU and the gait cycle percentage to at least one of a client device of the user and a database accessible via a communication network. The one or more processors can be programmed to execute instructions stored in the one or more memory units to instruct the EMS generator to generate a plurality of asymmetrical biphasic square pulses for transmission to electrodes of the one or more electrode arrays to provide the electrical stimulation to the limb of the user.

The one or more processors can also be programmed to execute instructions stored in the one or more memory units to map the gyroscope readings and the accelerometer readings to two periodic functions using the machine learning algorithm. In some embodiments, the machine learning algorithm can comprise one or more multilayer perceptron neural networks. The one or more processors can be programmed to execute additional instructions to calculate a phase angle from the two periodic functions and convert the phase angle to the gait cycle percentage. The one or more processors can be programmed to execute instructions stored in the one or more memory units to smooth out the two periodic functions using one or more low-pass filter functions prior to calculating the phase angle.

A method of modulating a movement of a limb of a user is also disclosed. The method comprises retrieving, using one or more processors, gyroscope readings and accelerometer readings from an inertial measurement unit (IMU). The one or more processors and the IMU can be part of a control unit further comprising a wireless communication module, one or more memory units, a portable power supply, and an electrical muscle stimulation (EMS) generator. A housing of the control unit can be coupled to at least one of one or more elastic wearable articles configured to be worn on the limb of the user.

The method can further comprise calculating, using the one or more processors, a gait cycle percentage by inputting the gyroscope readings and the accelerometer readings into a machine learning algorithm and instructing the EMS generator to provide electrical stimulation to the limb of the user via one or more electrode arrays based in part on the gait cycle percentage calculated. At least one of the one or more electrode arrays can be coupled to an inner surface of at least one of the one or more elastic wearable articles. The electrodes of the one or more electrode arrays can be in physical contact with the limb of the user when the one or more elastic wearable articles are worn by the user.

The method further comprises mapping, using the one or more processors, the gyroscope and accelerometer measurements to two periodic functions using the machine learning algorithm, smoothing out the two periodic functions using one or more low-pass filter functions, and calculating a phase angle from the two periodic functions, and converting the phase angle to the gait cycle percentage. The machine learning algorithm can comprise one or more multilayer perceptron neural networks.

In some embodiments, the one or more elastic wearable articles can comprise a first elastic sleeve and a second elastic sleeve. The first elastic sleeve can be configured to be worn on a thigh of the user and the second elastic sleeve can be configured to be worn on a lower leg of the user between a knee and an ankle of the user. The one or more electrode arrays can comprise at least a first upper leg array, a second upper leg array, a first lower leg array, and a second lower leg array. The first upper leg array and the second upper leg array can be coupled to the inner surface of the first elastic sleeve. The first upper leg array and the second upper leg array can be in physical contact with a skin surface in proximity to a hamstring of the user when the first elastic sleeve is worn on the thigh of the user. Moreover, the first lower leg array and the second lower leg array can be coupled to the inner surface of the second elastic sleeve. The first lower leg array and the second lower leg array can be in physical contact with the skin surface in proximity to a tibialis anterior of the user when the second elastic sleeve is worn on the lower leg of the user.

Alternatively, the one or more elastic wearable articles can comprise one elastic sleeve or cuff configured to be worn on a lower leg of the user between a knee and an ankle of the user. The one or more electrode arrays can comprise a first lower leg array and a second lower leg array coupled to the inner surface of the elastic sleeve. At least one of the first lower leg array and the second lower leg array can be in physical contact with the skin surface in proximity to a tibialis anterior of the user when the elastic sleeve is worn on the lower leg of the user.

The method can further comprise transmitting, using the wireless communication module, readings from the IMU and the gait cycle percentage calculated to at least one of a client device of the user and a database accessible via a communication network. Moreover, the method can further comprise instructing the EMS generator to generate a plurality of asymmetrical biphasic square pulses for transmission to electrodes of the one or more electrode arrays to provide the electrical stimulation to the nerves and muscles of the limb of the user.

The method can further comprise mapping gyroscope readings and accelerometer readings to three-dimensional angles of at least one of a hip, a knee, and a foot of the user throughout a gait cycle. The method can also comprise determining at least one of a foot strike pattern, a foot inclination angle at initial contact, a tibia angle at loading response, a hip extension during late stance, a trunk lean, a heel eversion, a foot progression angle, a pelvic drop, a knee flexion during stance, a stride length, a knee window, a vertical displacement of the center mass, and a heel whip of the user based in part on the gait cycle percentage calculated, the gyroscope readings, the accelerometer readings, and the mapped three-dimensional angles.

DETAILED DESCRIPTION

Figure 1A:
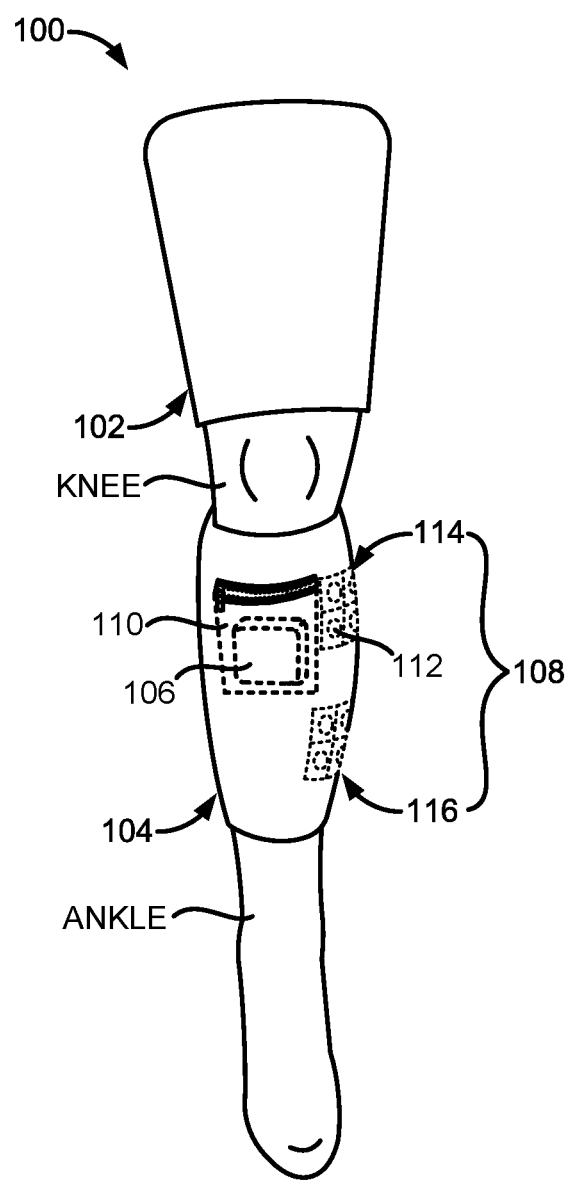
FIG. 1A illustrates a front view of one embodiment of a functional electrical simulation (FES) device for real-time gait modulation.

FIG. 1A illustrates a front view of one embodiment of a functional electrical simulation (FES) device 100 for real-time gait modulation. The device 100 can comprise one or more elastic wearable articles configured to be worn on a limb of a user. In some embodiments, the elastic wearable articles can comprise one or more elastic sleeves such as wearable compression sleeves. In other embodiments, the one or more elastic wearable articles can comprise elastic straps, elastic wrappings, elastic bands, or elastic clothing such as compression leggings, pants, shorts, socks, shirts, vests, bras, or a combination thereof. The elastic wearable article can be a compliant or pliant wearable article configured to cover, envelope, circumscribe, and/or extend over at least a segment of the user's limb(s). The elastic wearable article can be made in part of a lightweight synthetic fabric such as spandex (also known as Lycra® or elastane). The elastic wearable article can also comprise other synthetic or organic fabrics including nylon, polyester, cotton, or a combination thereof. More specifically, the nylon can be Cordura® nylon, oxford cloth nylon, or a combination thereof. In some embodiments, the elastic wearable articles can be made of materials having moisture wicking properties.

It has been discovered by the applicant that integrating an FES device 100 with a compression sleeve or other compressive wearable article can provide the added benefit of stabilizing the muscles of a user having a walking or mobility impairment. For example, an FES device 100 designed as a compression sleeve or other compressive wearable article can improve blood flow and stabilize muscles in addition to stimulating such muscles.

As shown in FIG. 1A, the device 100 can comprise two elastic sleeves (e.g., leg sleeves) including a first elastic sleeve 102 and a second elastic sleeve 104. The first elastic sleeve 102 can be configured to be worn on or cover at least part of an upper leg of the user. For example, the first elastic sleeve 102 can be configured to be worn on or cover at least part of a thigh of the user. The second elastic sleeve 104 can be configured to be worn on or cover at least part of a lower leg of the user. For example, the second elastic sleeve 104 can be configured to be worn on or cover at least part of the lower leg of the user between a knee (or patella/kneecap) and an ankle of the user. As shown in FIG. 1A, the knee of the user can be exposed when the device 100 comprises two elastic sleeves and the first elastic sleeve 102 is worn on a lower leg of the user and the second elastic sleeve 104 is worn on an upper leg of the user. One advantage of this design is the freedom of motion provided the user when the knee of the user is not constricted.

In the embodiments shown in FIG. 1A, the first elastic sleeve 102 and the second elastic sleeve 104 can be worn on the same leg of the user. In other embodiments not shown in the figure but contemplated by this disclosure, the first elastic sleeve 102 and the second elastic sleeve 104 can be worn on different legs of the user or on each leg of the user.

In other embodiments, the device 100 can comprise one elastic sleeve covering only the upper leg or only the lower leg of the user. In these embodiments, the device 100 can comprise only one of the first elastic sleeve 102 or the second elastic sleeve 104. In additional embodiments not shown in the figures but contemplated by this disclosure, the device 100 can comprise one long elastic sleeve covering part of the upper leg (e.g., part of the thigh) and part of the lower leg (e.g., part of the lower leg between the knee and the ankle) of the user.

The device 100 can also comprise a control unit 106 and one or more electrode arrays 108 coupled to the elastic wearable article. As shown in FIG. 1A, the control unit 106 can be detachably carried or detachably coupled to the elastic wearable article (e.g., any of the first elastic sleeve 102 or the second elastic sleeve 104). For example, the control unit 106 can be detachably carried by the elastic wearable article by being stored, positioned, or housed within a pocket or enclosure 110 of the elastic wearable article. As a more specific example, the pocket or enclosure 110 can be a zipper pocket sewn into or onto the elastic wearable article (e.g., any of the first elastic sleeve 102 or the second elastic sleeve 104). In other embodiments, the pocket or enclosure 110 can be a pocket, sachet, or enveloped enclosure configured to be closed and opened via a hook-and-loop fastener (e.g., Velcro®), a snap button fastener, a fold covering, a magnetic fastener, or a combination thereof. Although FIG. 1A shows the pocket or enclosure 110 sewn or otherwise coupled to the second elastic sleeve 104, it is contemplated by this disclosure that the pocket or enclosure 110 can also be sewn or otherwise coupled to the first elastic sleeve 102 and the control unit 106 can be detachably coupled or carried by the first elastic sleeve 102. The pocket or enclosure 110 can be sized to tightly or securely house or contain the control unit 106 such that the control unit 106 does not inadvertently shift or rock within the pocket or enclosure 110.

The control unit 106 can be detachably coupled or carried by the elastic wearable article to allow the elastic wearable article to be washed or cleaned when the control unit 106 is removed. In addition, the control unit 106 can be detachably coupled or carried by the elastic wearable article to allow for the control unit 106 to be updated or new control units 106 to be used with legacy wearable articles. In other embodiments not shown in the figures but contemplated by this disclosure, the control unit 106 can be detachably coupled to the outer surface or inner surface of the elastic wearable article via adhesives, a magnetic coupling mechanism, a latch or clasp, a snap fitting, or a combination thereof.

As shown in FIG. 1A, the control unit 106 can be positioned on the front or anterior side of the lower leg of the user and below the knee of the user. For example, the control unit 106 can be securely housed or held by a pocket or enclosure 110 positioned on the front or anterior side of the lower leg of the user slightly below the knee of the user. Since the control unit 106 is housed or encapsulated by the pocket or enclosure 110, the control unit 106 is shown in FIG. 1A in broken lines.

As will be discussed in more detail in the following sections, the control unit 106 can comprise at least a gyroscope 314, an accelerometer 316, a magnetometer 318, or a combination thereof (see FIG. 3). One unexpected discovery made by the applicant is that gyroscope readings obtained from a gyroscope 314 positioned on the anterior side of the lower leg of the user below the knee of the user results in more robust input data that can be introduced to a machine learning algorithm 700 (see FIG. 7) to map to periodic functions used to calculate a more accurate gait cycle percentage 500 (see FIG. 5).

In other embodiments not shown in the figures but contemplated by this disclosure, the control unit 106 can also be positioned anywhere on the user's leg, including on the back of the lower leg of the user (in proximity to the calf or gastrocnemius) of the user. Moreover, the control unit 106 can also be positioned on the front of the upper leg of the user above the patella or knee of the user.

The device 100 can also comprise one or more electrode arrays 108 in electrical communication with the control unit 106. For example, the one or more electrode arrays 108 can be in electrical communication with an electrical muscle stimulation (EMS) generator 310 (see FIG. 3) of the control unit 106. The one or more electrode arrays 108 can be in electrical communication with the control unit 106 via a number of conductive wires, electrical traces, conductive fibers, or a combination thereof. The conductive wires, electrical traces, conductive fibers, or a combination thereof can be embedded within layers of the elastic wearable article or interwoven with fibers used to make the elastic wearable article.

Each of the electrode arrays 108 can be comprised of a plurality electrodes 112 in proximity to other electrodes 112. For example, as shown in FIG. 1A, the electrodes 112 of each of the electrode arrays 108 can be arranged in a grid pattern. In other embodiments, the electrodes 112 of each of the electrode arrays 108 can be arranged in a circular pattern, an oval pattern, a spiral pattern, a linear pattern, a zig-zig pattern, a rhombus pattern, a triangular pattern or another polygonal pattern, or a combination thereof.

Each of the electrodes 112 can comprise a number of layers including a substrate or contact layer, one or more conductive layers, and a connector layer. The conductive layers can be made in part of a metal, metal chloride, or metal oxide. For example, the conductive layers can be made in part or comprise silver or silver chloride. In some embodiments, a silver mesh layer can be shared by all of the electrodes 112 of one electrode array 108. The substrate or contact layer can be biocompatible polymeric layer. The substrate or contact layer can physically contact the skin surface of the user. For example, the substrate or contact layer can comprise a layer of cross-linked copolymers such as a hydrogel layer. In these and other embodiments, the substrate or contact layer can also require that a conductive gel or conductive solution coat or cover the skin surface of the user, the substrate or contact layer, or a combination thereof before operating the device 100. In these and other embodiments, the substrate or contact layer can be a sponge made conductive with an ionic solution. The connector layer can comprise a number of receptors or connectors configured to connect the electrodes 112 to wires, traces, or fibers leading to components within the control unit 106.

The electrodes 112 of the one or more electrode arrays 108 can be coupled to an inner surface of the elastic wearable article (e.g., the first elastic sleeve 102, the second elastic sleeve 104, or a combination thereof). For example, the electrode arrays 108 can be coupled to the inner surface of the elastic wearable article by adhesives, clips, straps, hook-and-loop fasteners, stitches (e.g., sewn into the elastic wearable article), or a combination thereof. The electrodes 112 can be positioned such that the substrate or contact layer of the electrodes 112 is in physical contact with a skin surface of the user when the user wears or puts on the elastic wearable article. In these and other embodiments, any of the electrodes 112 of the electrode arrays 108 can be detached or separated from the elastic wearable article. This can allow the elastic wearable article to be washed or cleaned and allow for worn or malfunctioning electrodes 112 to be replaced.

FIG. 1A illustrates that the second elastic sleeve 104 can comprise at least a first lower leg array 114 and a second lower leg array 116. The first lower leg array 114 can be positioned or arranged superior to or above the second lower leg array 116 when the second elastic sleeve 104 is worn by the user. Although two electrode arrays 108 are shown coupled to the second elastic sleeve 104, it is contemplated by this disclosure that any number of electrode arrays 108 can be coupled to the second elastic sleeve 104 including, but not limited to, three electrode arrays 108, four electrode arrays 108, five electrode arrays 108, six electrode arrays 108, seven electrode arrays 108, eight electrode arrays 108, nine electrode arrays 108, and ten or more electrode arrays 108 distributed over various neuromuscular targets on the body of the user.

Figure 1B:
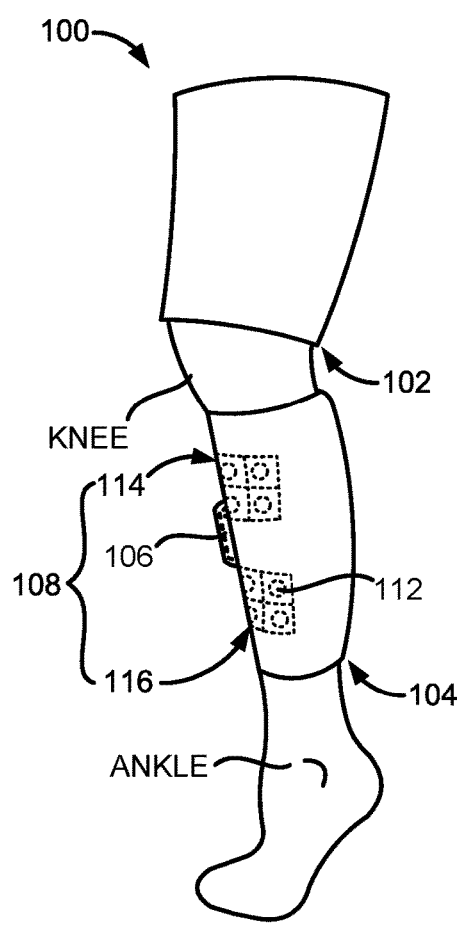
FIG. 1B illustrates a side perspective view of one embodiment of the FES device.

FIG. 1B illustrates a side perspective view of the device 100 shown in FIG. 1A. As shown in FIGS. 1A and 1B, the first lower leg array 114 and the second lower leg array 116 can be positioned in proximity to a tibialis anterior muscle of the user when the second elastic sleeve 104 is worn on the lower leg of the user (e.g., between the knee or patella of the user and the ankle). For example, the first lower leg array 114 and the second lower leg array 116 can be positioned such that the substrate or contact surface of the electrodes 112 within these arrays physically contact the skin surface in proximity to a tibialis anterior muscle of the user. Since the tibialis anterior muscles are innervated in part by the deep fibular nerve (also known as the deep peroneal nerve), providing electrical stimulation to the deep fibular nerve (or deep peroneal nerve) via electrodes 112 of the first lower leg array 114, the second lower leg array 116, or a combination thereof positioned in proximity to the tibialis anterior muscles can cause dorsiflexion of the foot of the user. As will be discussed in more detail in the following sections, terminating electrical stimulation to the deep fibular nerve (or deep peroneal nerve) can result in the user relaxing the dorsiflexion motion.

Figure 1C:
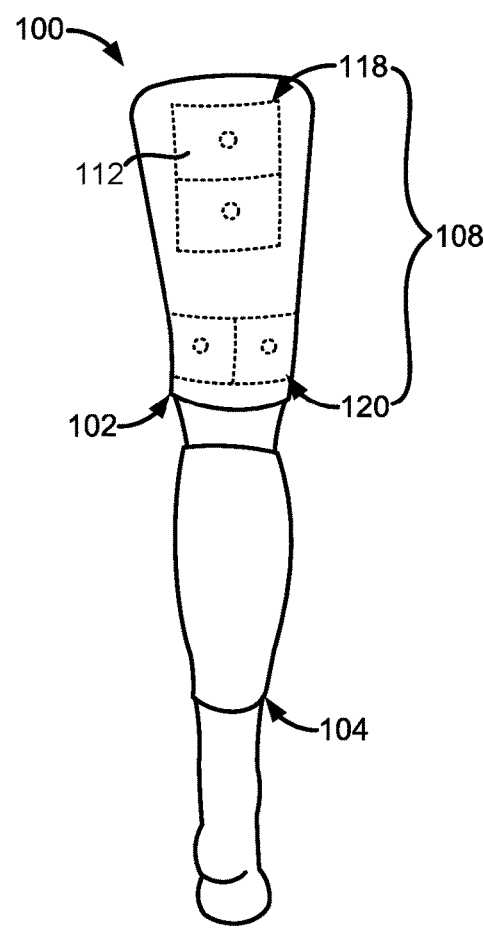
FIG. 1C illustrates a rear view of one embodiment of the FES device.

FIG. 1C illustrates a rear view of the device 100 shown in FIGS. 1A and 1B. As depicted in FIG. 1C, the device 100 can further comprise a first upper leg array 118 and a second upper leg array 120. At least one of the first upper leg array 118 and the second upper leg array 120 can be coupled or otherwise attached to an inner surface of the first elastic sleeve 102. The first upper leg array 118 can be positioned above or superior to the second upper leg array 120 when the first elastic sleeve 102 is worn by the user. The first upper leg array 118 and the second upper leg array 120 can be positioned in proximity to a hamstring muscle of the user when the first elastic sleeve 102 is worn on a thigh of the user. For example, the first upper leg array 118 and the second upper leg array 120 can be positioned such that the substrate or contact surface of the electrodes 112 within these arrays physically contact the skin surface in proximity to the hamstring muscles of the user. The hamstring muscles are innervated in part by the tibial nerve and the sciatic nerve. Providing electrical stimulation to the tibial nerve, the sciatic nerve, or a combination thereof via electrodes 112 of the first upper leg array 118, the second upper leg array 120, or a combination thereof in proximity to the hamstring muscles can cause plantarflexion of the foot of the user. Terminating electrical stimulation to such nerve(s) can result in the user ceasing the plantarflexion motion.

As will be discussed in more detail in the following sections, selective activation of electrodes 112 of one or more electrode arrays 108 (e.g., the first upper leg array 118, the second upper leg array 120, the first lower leg array 114, the second lower leg array 116, or a combination thereof) can provide electrical stimulation to the neuromuscular system of the leg and foot of the user and cause the leg and foot of the user to move in such a way as to enhance or correct (or make up for any impairments of) the gait of the user.

Although two electrode arrays 108 are shown coupled to the first elastic sleeve 102, it is contemplated by this disclosure that any number of electrode arrays 108 can be coupled to the first elastic sleeve 102 including, but not limited to, three electrode arrays 108, four electrode arrays 108, five electrode arrays 108, six electrode arrays 108, seven electrode arrays 108, eight electrode arrays 108, nine electrode arrays 108, and ten or more electrode arrays 108.

Moreover, FIG. 1C illustrates that the electrodes 112 of the first upper leg array 118 and the second upper leg array 120 can be bigger in size (i.e., larger electrode contact surface area or the arrays cover more skin surface area) than the electrodes 112 of the first lower leg array 114 or the second lower leg array 116. The electrodes 112 of the first upper leg array 118 and the second upper leg array 120 can be bigger in size due to the size disparity between the hamstring muscles and the tibialis anterior muscles.

Figure 1D:
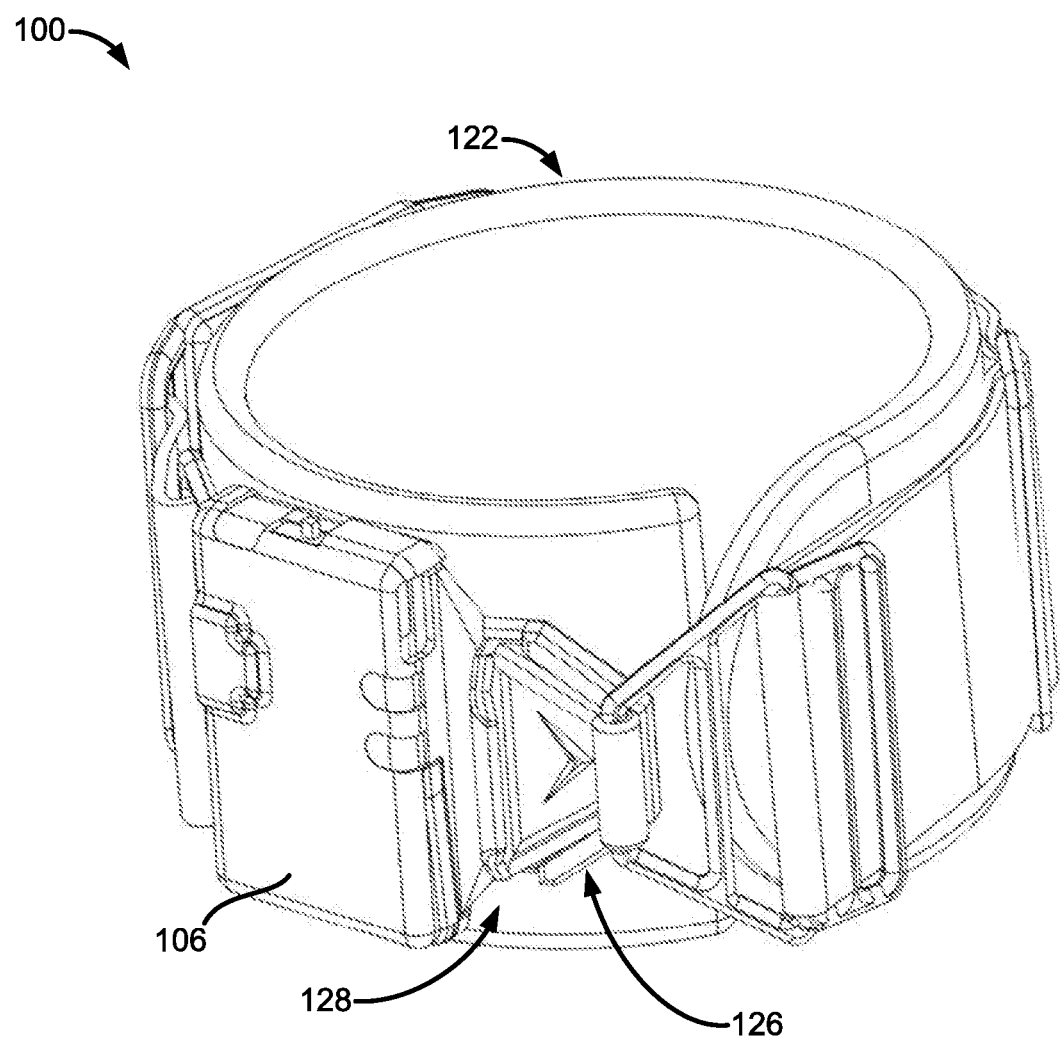
FIG. 1D illustrates a perspective view of another embodiment of the FES device.
Figure 1E:
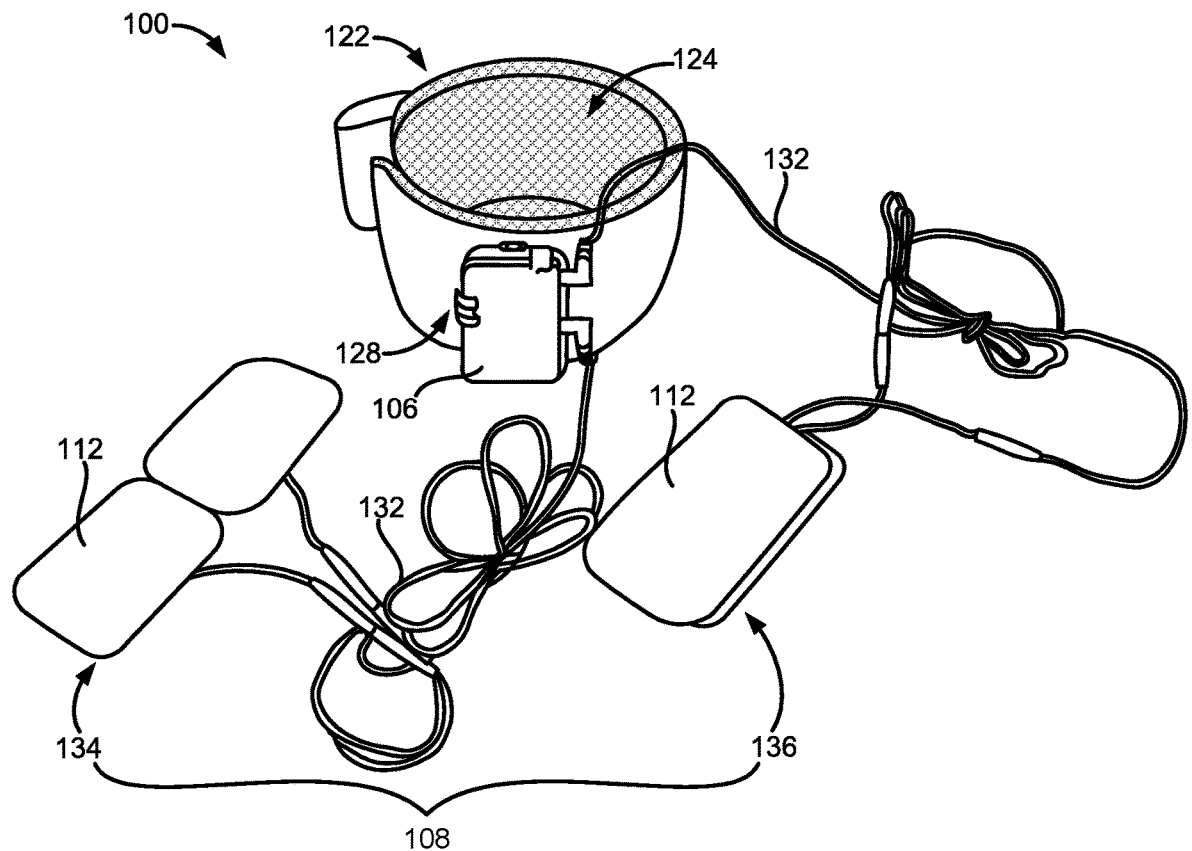
FIG. 1E illustrates another embodiment of the FES device connected to wearable electrodes.
Figure 1F:
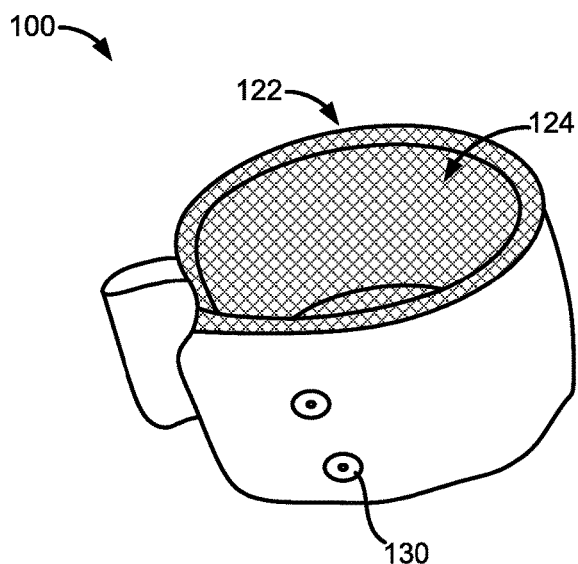
FIG. 1F illustrates a wearable cuff of the FES device shown in FIG. 1E.

FIGS. 1D to 1F illustrate other embodiments of the functional electrical stimulation device 100 for real-time gait modulation. The device 100 can comprise one or more elastic wearable articles configured to be worn on a limb of a user. In these embodiments, the elastic wearable articles can comprise a strap or cuff 122 to be worn on a leg of the user.

The strap or cuff 122 can be made in part of a semi-rigid thermoplastic polyurethane (TPU) core covered by a textile or fabric-type material 124 (see FIGS. 1E and 1F). In some embodiments, the textile or fabric-type material can be a mesh fabric.

The strap or cuff 122 can be secured to the limb of the user using a fastening mechanism 126. In some embodiments, the fastening mechanism 126 can comprise an elastic strap or clip. In these and other embodiments, the fastening mechanism 126 can comprise a magnetic latching mechanism. The fastening mechanism 126 can be configured such that the fastening mechanism 126 can be fastened or unfastened with a single hand of the user. One rationale for a fastening mechanism 126 that is operable by a single hand of the user is that many users of the device 100 may have hemiparesis, a condition whereby the ipsilateral hand may have a similar degree of paralysis as the leg on which the strap or cuff 122 is to be worn.

As shown in FIGS. 1D and 1E, the control unit 106 can be detachably or removably coupled to an exterior surface 128 or outer side of the device 100. For example, FIG. 1F illustrates that the control unit 106 can be detachably or removably coupled to the device 100 via snap fasteners 130 positioned on the exterior surface 128 of the strap or cuff 122.

FIG. 1E also illustrates that the device 100 can comprise one or more electrode arrays 108 in electrical communication with the control unit 106. For example, the electrodes 112 of the electrode array(s) 108 can be in electrical communication with the EMS generator 310 (see FIG. 3) of the control unit 106. The electrodes 112 of the electrode array(s) 108 can be 2 in electrical communication with the control unit 106 via a number of conductive leads or lead cables 132, electrical traces, conductive fibers, or a combination thereof.

The electrode arrays 108 can comprise an upper leg electrode array 134 and a lower leg electrode array 136. The control unit 106 can control a plurality of electrode arrays 108 connected by leads or lead cables 132 to the control unit 106. The electrode arrays 108 can be distributed across different muscle groups of the user. The device 100 and methods disclosed herein can allow any muscle to be stimulated with appropriate timing relative to the gait cycle. The device 100 can also be configured to output to one or more stimulation channels (e.g., two independent stimulation channels). For example, one of the channels can be electrically coupled to or in electrical communication with electrodes 112 of the lower leg electrode array 136 via leads embedded within the elastic wearable article (e.g., a fabric portion of the cuff 122) to stimulate the tibialis anterior muscle or common peroneal nerve. Also, in this example, a second channel can be electrically coupled to or in electrical communication with the electrodes 112 of the upper leg electrode array 134 via lead cables 132 extending from the control unit 106. The upper leg electrode array 134 can be used to stimulate the hamstring muscles or the tibial nerve or sciatic nerve of the user. The two channels can be programmed independently such that amplitude, waveform, and gait phase (on-off timing) can all be specified independently.

In some embodiments, the control unit 106 can comprise a user interface or wired control panel comprising a plurality of multi-colored LED lights and at least one push-button or switch configured to allow the device 100 to be turned on/off and stimulation settings (e.g., amplitude, frequency, and mode) to be adjusted. In certain embodiments, the control panel can comprise a plurality of push-buttons or switches (e.g., three push-buttons or switches). In these and other embodiments, the device 100 can be controlled by a client device (e.g., a smartphone, tablet computer, or smartwatch) of the user in wireless communication with the control unit 106. A user can turn on/off the device 100, adjust the stimulation settings (e.g., amplitude, frequency, and mode), review usage metrics, and upload data to a database using the client device in wireless communication with the control unit 106.

Figure 1G:
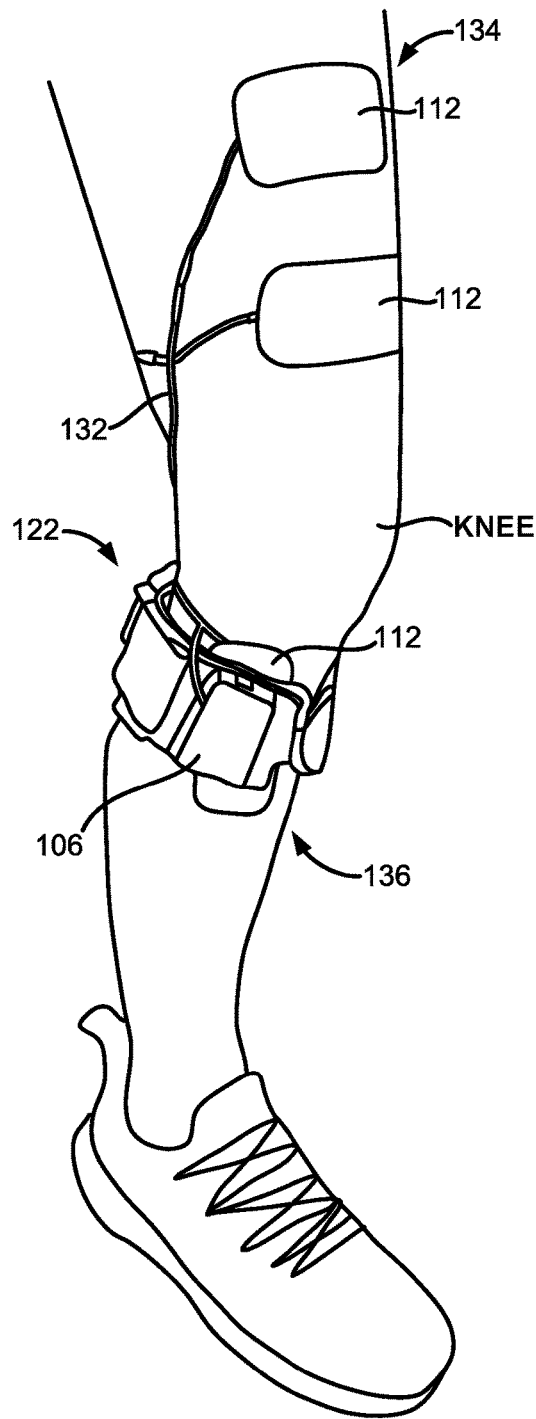
FIGS. 1G and 1H illustrate side and rear perspective views of an embodiment of the FES device worn on a leg of a user.
Figure 1H:
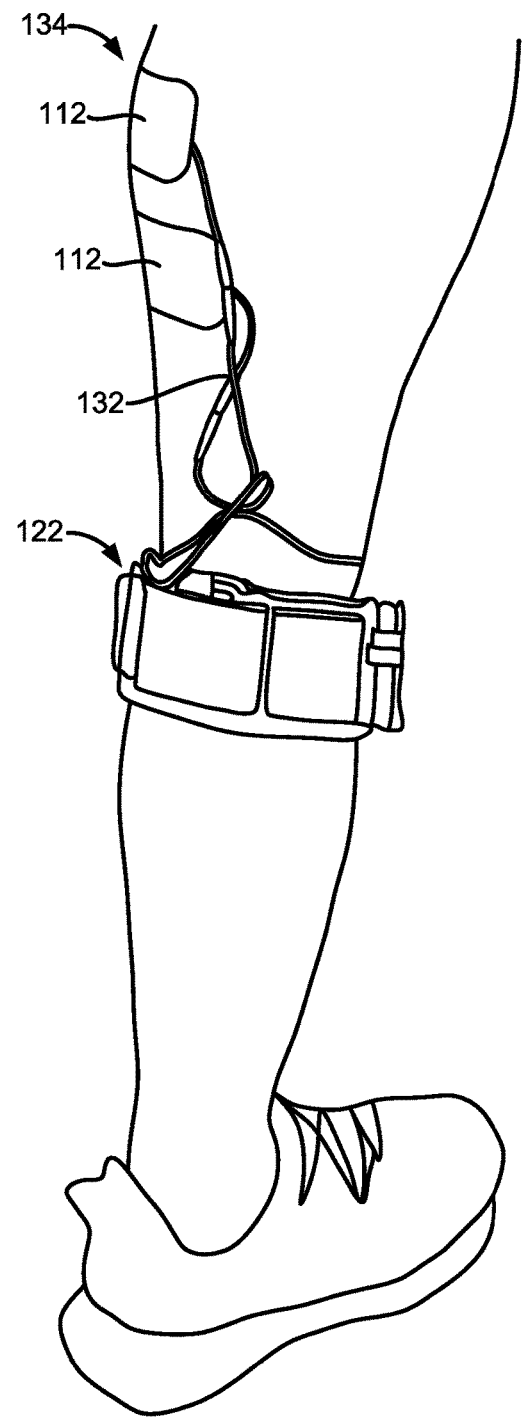

FIGS. 1G and 1H illustrate the FES device 100 comprising the strap or cuff 122 worn on a leg of the user. The strap or cuff can be worn on a lower leg of the user between a knee and an ankle of the user (e.g., right under the knee of the user). An upper leg electrode array 134 and a lower leg electrode array 136 can be electrically coupled to or in electrical communication with the control unit 106 via one or more lead cables 132 or leads. The upper leg electrode array 134 can be adhered (e.g., via biocompatible adhesives, gels, stick pads, straps, bands, etc.) to the hamstring muscles, the quadricep muscles, or the rectus femoris muscle of the user. As previously discussed, the hamstring muscles are innervated in part by the tibial nerve and the sciatic nerve. Providing electrical stimulation to the tibial nerve, the sciatic nerve, or a combination thereof via electrodes 112 of the upper leg array 134 can cause plantarflexion of the foot of the user.

The lower leg electrode array 136 can be adhered (e.g., via biocompatible adhesives, gels, stick pads, straps, bands, etc.) to the tibialis anterior muscles of the user. As previously discussed, the tibialis anterior muscles are innervated in part by the deep fibular nerve (also known as the deep peroneal nerve). Providing electrical stimulation to the deep fibular nerve (or deep peroneal nerve) via electrodes 112 of the lower leg array 136 can cause dorsiflexion of the foot of the user. Terminating such electrical stimulation to the deep fibular nerve (or deep peroneal nerve) can cause the user to relax the dorsiflexion motion.

Figure 2A:
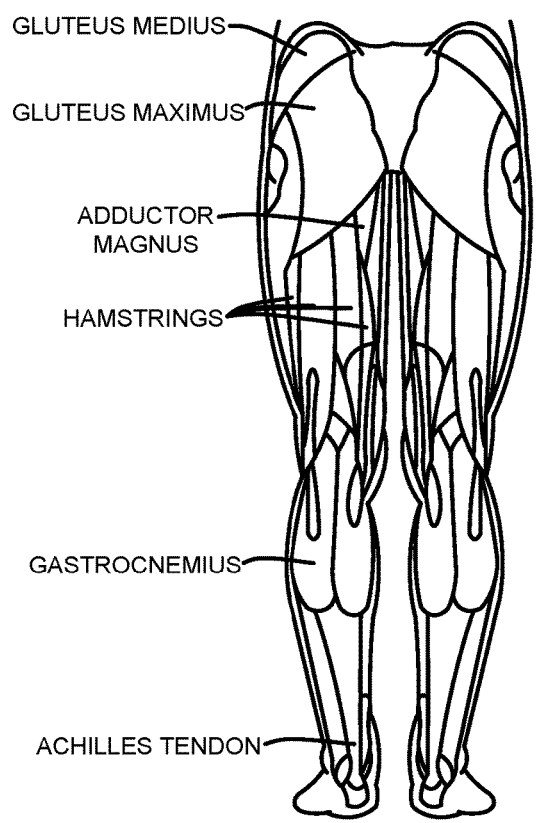
FIGS. 2A and 2B are rear and front views, respectively, of schematic drawings of muscles of the human leg.
Figure 2B:
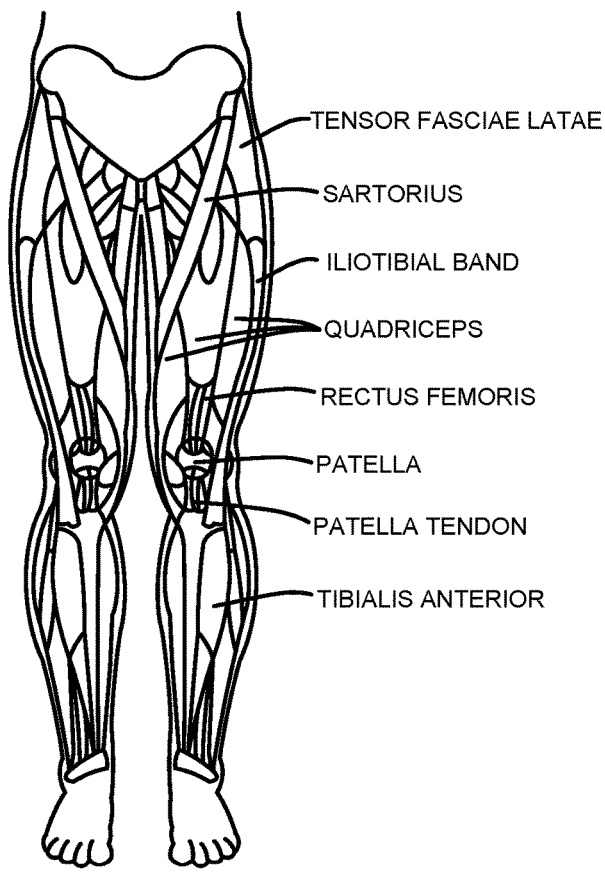

FIGS. 2A and 2B are schematic drawings showing rear and front views, respectively, of muscles of the human leg. Although FIGS. 1A, 1B, 1C, 1G, and 1H illustrate the electrode arrays 108 positioned in proximity to the tibialis anterior and hamstring muscles of the user, it is contemplated by this disclosure that one or more electrode arrays 108 can also be positioned in proximity to the gastrocnemius (or calf) muscle, the quadricep muscles, and the rectus femoris muscle of the user. For example, at least one electrode array 108 can be coupled or otherwise attached to an anterior portion or side of the inner surface of the first elastic sleeve 102. Also, for example, at least one electrode array 108 can be coupled or otherwise attached to a posterior portion or side of the inner surface of the second elastic sleeve 104. Moreover, it is contemplated by this disclosure that any of the muscles shown in FIGS. 2A and 2B, and nerves innervating such muscles, can be stimulated by electrode arrays 108 coupled or otherwise attached to the elastic wearable article.

Figure 3:
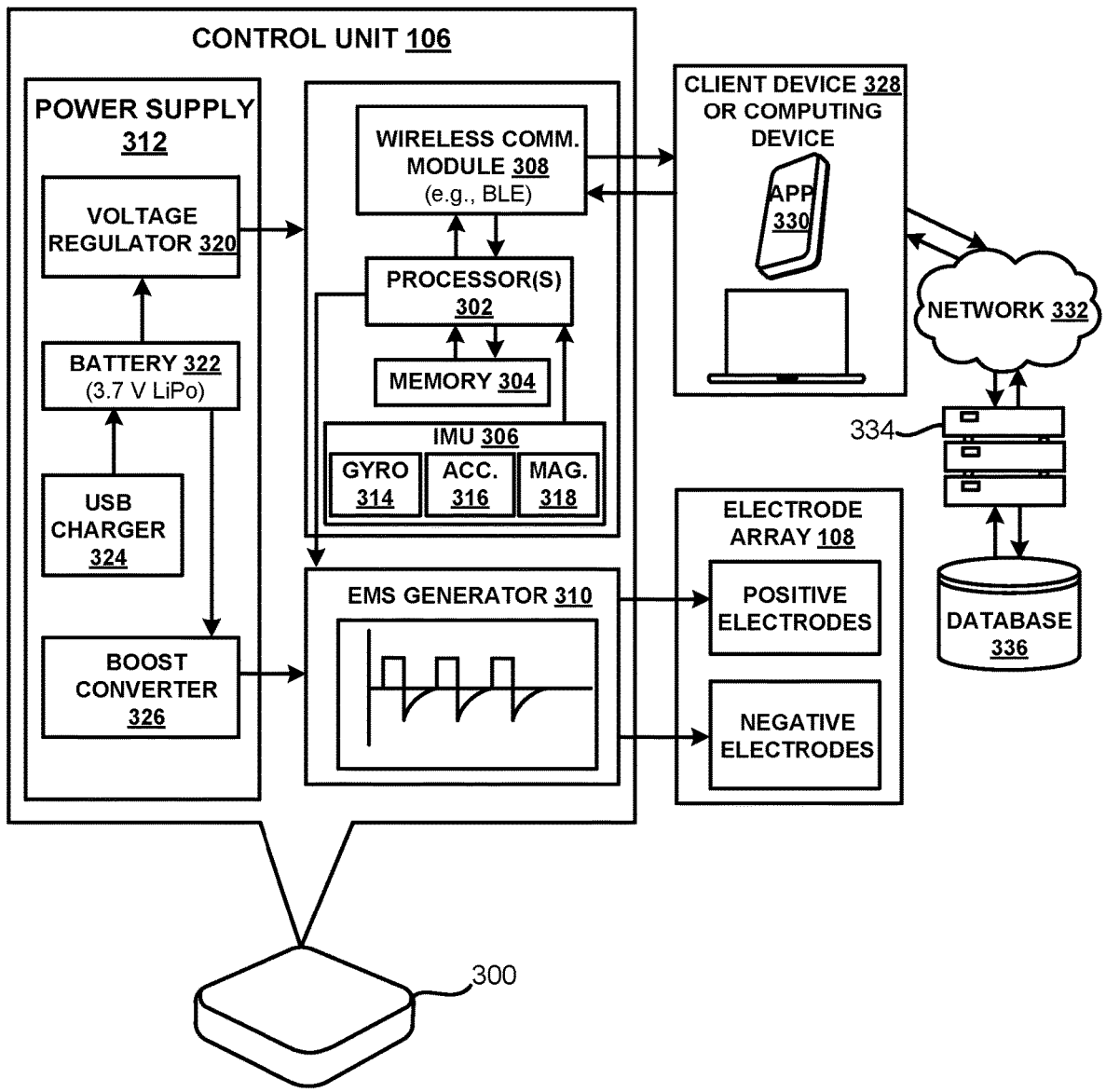
FIG. 3 is a schematic showing certain electronic components of the FES device.

FIG. 3 is a schematic showing certain electronic components of the FES device 100. The electronic components can be housed within a device housing 300. The device housing 300 can comprise a rigid shell or outer layer and can contain one or more printed circuit boards (PCBs) having electronic components affixed or electrically connected to the PCBs.

The device housing 300 can be made in part of a polymeric material, a metallic material, or a combination thereof. For example, the device housing 300 can be made in part of acrylonitrile butadiene styrene (ABS) plastic, polylactic acid (PLA), polycarbonate (PC), polypropylene (PP), polyvinyl chloride (PVC), poly(methyl methacrylate) (PMMA), polyamide (PA), polystyrene, thermoplastic elastomer (TPE), polyethylene terephthalate (PET), carbon fibers, rubber, thermoplastic rubber, nitrile butadiene rubber, stainless steel, aluminum, or a combination thereof. The rigid shell or outer layer of the device housing 300 should be capable of protecting the electronic components housed within the device housing 300 from unintentional damage or routine stress and wear.

The device housing 300 can be substantially shaped as a cuboid or cuboid with rounded edges. In other embodiments, the device housing 300 can be substantially shaped as an ovoid, a conic or frustoconic, a cylinder, a dome or hemisphere, a pyramid or truncated pyramid, or a combination thereof. For example, the device housing 300 can be a cuboid having a length dimension of between about 5.0 cm to about 10.0 cm, a width dimension of between about 3.0 cm to about 10.0 cm, and a height dimension of between about 0.5 cm to about 5.0 cm. As previously described, the device housing 300 can be small enough to tightly or securely fit within a pocket or enclosure 110 sewn into, onto, or otherwise coupled to the wearable elastic article.

The control unit 106 can comprise one or more processors 302, one or more memory units 304 coupled to the one or more processors 302 and configured to be accessible to the one or more processors 302, an inertial measurement unit (IMU) 306, a wireless communication module 308, an electrical muscle stimulation (EMS) generator 310, and a portable power supply 312.

The one or more processors 302 can be 32-bit processors or 64-bit processors. The one or more processors 302 can be any processor capable of operating at a clock frequency of at least 12 MHz. For example, at least one of the one or more processors 302 can be a 48 MHz processor. In other embodiments, the one or more processors 302 can be 160 MHz processors or 240 MHz processors. As a more specific example, at least one of the one or more processors 302 can be an ARM microprocessor.

The memory units 304 can comprise read-only memory (ROM) (e.g., up to 448 kB of ROM), on-chip static random-access memory (SRAM) (e.g., up to 520 kB of SRAM), flash memory (e.g., up to 16 MB of flash memory), or a combination thereof.

The one or more processors 302 can be programmed to execute instructions stored in the one or more memory units 304. For example, the memory units 304 can store software instructions or firmware instructions (e.g., any of the method steps or instructions disclosed herein) written in the C++ programming language, C programming language, Java programming language, Python programming language, or a combination thereof.

The wireless communication module 308 can comprise a WiFi module, a Bluetooth™ module, a Zigbee™ module, a near-field communication (NFC) module, a cellular communication module, or a combination thereof. For example, the wireless communication module 308 can be a Bluetooth™ module or Bluetooth™ Low Energy (BLE) module and support a number of Bluetooth™ communication protocols (e.g., IEEE 802.15.1) or Bluetooth Smart™ protocols. In these and other embodiments, the wireless communication module 308 can also be or comprise a WiFi module and the WiFi module can support a number of WiFi communication protocols including the IEEE 802.11b protocol, the IEEE 802.11g protocol, the IEEE 802.1 in protocol, or a combination thereof. For example, the WiFi module can allow the device 100 to wirelessly connect with a wireless networking device (e.g. wireless router, modem, or gateway) to communicate with one or more servers or client devices over a wide area network (WAN), such as the Internet. In additional embodiments, the wireless communication module 308 can be a cellular communication module and the cellular communication module can support a number of cellular communication protocols or standards including communication over 3G, 4G, or 5G cellular networks.

The IMU 306 can comprise a gyroscope 314, an accelerometer 316, and a magnetometer 318. In one embodiment, the IMU 306 can be a 9-degrees of freedom (9DoF) IMU configured to capture nine distinct motion or orientation related data including 3 degrees each of acceleration, magnetic orientation, and angular velocity. For example, the gyroscope 314 can be a user-programmable 3-axis gyroscope configured to capture angular velocity up to ±2,000 degrees per second (°/sec). The accelerometer 316 can be a 3-axis accelerometer configured to capture acceleration data up to ±16 g. The magnetometer 318 can be a 3-axis magnetometer configured to capture magnetic orientation up to ±8.1 gauss. As described previously, the IMU 306 can capture motion and orientation data when the control unit 106 is positioned on an anterior side of the lower leg of the user below the knee of the user. One unexpected discovery made by the applicant is that gyroscope readings or data collected when the IMU/gyroscope is located on the anterior side of the lower leg of the user below the knee could be inputted into one or more machine learning algorithms 700 (e.g., multilayer perceptron neural networks) to accurately predict the gait cycle percentage of the leg of the user in motion. In other embodiments, the control unit 106 can also be positioned on a posterior side of the lower leg (above the gastrocnemius or calf muscle) below the knee of the user or on an anterior side of the thigh of the user. Usage of the gyroscope readings or data will be discussed in more detail in the following sections.

The control unit 106 can also comprise an EMS generator 310 and a portable power supply 312. The portable power supply 312 can further comprise a voltage regulator 320 configured to regulate voltage provided to the processors 302, memory units 304, wireless communication module 308, and the IMU 306, a battery 322, a charging component 324, and a boost converter 326. In some embodiments, the battery 322 can be a lithium polymer (LiPo) battery. For example, the battery 322 can be a 3.7 V LiPo battery. The battery 322 can be charged by a charging component 324 such as a USB charger. The boost converter can be a direct-current (DC) low-voltage to high-voltage converter (e.g., a DC 12V to DC 120V converter). Other amplifying techniques or components can also be used including voltage pump multipliers or transformers.

The EMS generator 310 can be electrically coupled to or in electrical communication (via conductive wires, traces, fibers, circuits, or a combination thereof) with electrodes 112 of the electrode arrays 108. The EMS generator 310 can be configured to transmit an electrical current resulting from a voltage generated by the power supply 312 to the electrodes 112 of the electrode array 108 in order to stimulate one or more nerves and/or muscles of the user. The EMS generator 310 can vary the stimulation parameters as to alter the bioresponse.

FIG. 3 also illustrates that the wireless communication module 308 can transmit data or readings obtained from the IMU 306, the memory units 304, or a combination thereof to a client device 328 over a short-range communication protocol. For example, the short-range communication protocol can be a Bluetooth™ protocol, a wireless fidelity (WiFi) (IEEE 802.11) communication protocol, an NFC protocol, or a combination thereof.

The client device 100 can be or refer to a portable electronic device such as a smartphone, a tablet computer, a laptop computer, a smartwatch, a fitness tracker, or a combination thereof. In other embodiments, the client device 100 can be or refer to a desktop computer, a smart television, a smart home appliance, or a combination thereof.

The client device 100 can run a software application 330 such as a mobile application (e.g., an iOS™ application or Android™ application) to interface with the device 100 and calibrate certain components of the device 100. For example, a user first using the FES device 100 can calibrate or set the stimulation strength and locations of electrodes 112 activated by the device 100. In one embodiment, a user can set the (1) max amplitude (e.g., between about 20 mA to about 80 mA), (2) frequency (e.g., between about 30 Hz to about 40 Hz), (3) pulse duration (e.g., between about 50 μs to about 300 μs), and/or (4) interpulse duration (e.g., between about 10 μs to about 50 μs, or about 20 Hz to about 100 Hz) of the current pulses sent to the electrodes 112 of the electrode array 108. As a more specific example, the user can select a current pulse having an amplitude of about 20 mA and a frequency of about 40 Hz. Alternatively, the user can select a current pulse having an amplitude of about 40 mA and a frequency of about 30 Hz.

In these and other embodiments, the user can also select the pair of electrodes 112 to be activated or used for stimulation. For example, the user can select two electrodes 112 diagonal or lateral to one another on the first lower leg array 114 to be used to stimulate the tibialis anterior muscle (and deep fibular nerve or deep peroneal nerve) of the user. As another example, the user can select two electrodes vertically aligned with one another on the first upper leg array 118 to be used to stimulate the hamstrings and tibial nerve of the user. The user can customize the electrode positions and stimulation strengths based on personal preference, comfort, or at the direction/suggestion of a physical therapist, physician, or other medical professional. The user can select the electrode locations (i.e., the pair of electrodes 112) and the stimulation strength using a graphic user interface (GUI) presented through the software application 330. The software application 330 can also present or visualize data or readings (through one or more GUI screens) captured by the components of the IMU 306 or calculated by the one or more processors 302.

As shown in FIG. 3, the client device 100 can also communicate with one or more servers 334 or access one or more databases 336 over one or more networks 332. The networks 332 can comprise or refer to one or more wide area networks (WANs) such as the Internet or other smaller WANs, wireless local area networks (WLANs), local area networks (LANs), wireless personal area networks (WPANs), system-area networks (SANs), metropolitan area networks (MANs), campus area networks (CANs), enterprise private networks (EPNs), virtual private networks (VPNs), multi-hop networks, or a combination thereof. The client device 100 or the servers 334 can connect to the networks 332 using any number of wired connections (e.g., Ethernet, fiber optic cables, etc.) and/or wireless connections established using a wireless communication protocol or standard such as a 3G wireless communication standard, a 4G wireless communication standard, a 5G wireless communication standard, a long-term evolution (LTE) wireless communication standard, a WiFi communication protocol, or a combination thereof.

The one or more servers 334 can comprise or refer to one or more centralized or stand-alone servers, de-centralized servers, or a combination thereof. For example, the one or more servers 334 can comprise or refer to a cloud computing resource, a virtualized computing resource, a part of a server farm, a server cluster, or a combination thereof. In some embodiments, the one or more servers 334 can take the form of a rack-mounted server, a blade server, a mainframe, a dedicated desktop or laptop computer, a portion thereof, one or more processors or processors cores therein, or a combination thereof.

In some embodiments, the database 336 can be a relational database such as a MySQL™ database. In other embodiments, the database 336 can be a NoSQL database such as a MongoDB™ database. In further embodiments, the database 336 can be a column-oriented or key-value database.

The device 100 can off-load processing to the client device 100, the one or more servers 334, or a combination thereof. For example, the device 100 can off-load calculation of certain walking metrics to the processors of the client device 100, the one or more servers 334, or a combination thereof. The device 100 can also transmit data, readings, or calculations to the memory of the client device 100, the one or more servers 334, or the database 336. The device 100 can also retrieve past or historical data, readings, or calculations stored in the memory of the client device 100, the one or more servers 334, or the database 336.

As a more specific example, one or more processors 302 of the device 100 can be programmed to execute instructions stored in the one or more memory units 304 to retrieve accelerometer readings from the accelerometer 316 of the IMU 306. Once such readings are retrieved, the device 100 can transmit the readings to the client device 100 or the one or more servers 334 to map these accelerometer readings (along with gyroscope readings) to three-dimensional angles of at least one of a hip, a knee, and a foot of the user through a gait cycle of the user. Moreover, the client device 100 and one or more servers 334 can determine at least one of a (1) foot strike pattern, (2) a foot inclination angle at initial contact, (3) a tibia angle at loading response, (4) a hip extension during late stance, (5) a trunk lean, (6) a heel eversion, (7) a foot progression angle, (8) a pelvic drop, (9) a knee flexion during stance, (10) a stride length, (11) a knee window, (12) a vertical displacement of the center mass, and (13) a heel whip of the user based in part on the mapped three-dimensional angles, the accelerometer readings, the gyroscope readings, and the gait cycle percentages 500 (see FIG. 5) calculated. The client device 100 can also display or visualize data concerning any of the (1) foot strike pattern, (2) the foot inclination angle at initial contact, (3) the tibia angle at loading response, (4) the hip extension during late stance, (5) the trunk lean, (6) the heel eversion, (7) the foot progression angle, (8) the pelvic drop, (9) the knee flexion during stance, (10) the stride length, (11) the knee window, (12) the vertical displacement of the center mass, and (13) the heel whip of the user through one or more GUIs generated by the software application 330.

In other embodiments, the one or more processors 302 of the device 100 can be programmed to execute instructions to map the accelerometer readings from the accelerometer 316 to three-dimensional angles of at least one of a hip, a knee, and a foot of the user through a gait cycle of the user. In these embodiments, the one or more processors 302 of the device 100 can also be programmed to execute instructions to determine at least one of a (1) foot strike pattern, (2) a foot inclination angle at initial contact, (3) a tibia angle at loading response, (4) a hip extension during late stance, (5) a trunk lean, (6) a heel eversion, (7) a foot progression angle, (8) a pelvic drop, (9) a knee flexion during stance, (10) a stride length, (11) a knee window, (12) a vertical displacement of the center mass, and (13) a heel whip of the user based in part on the mapped three-dimensional angles, the accelerometer readings, the gyroscope readings, and the gait cycle percentages 500 calculated.

Figure 4:
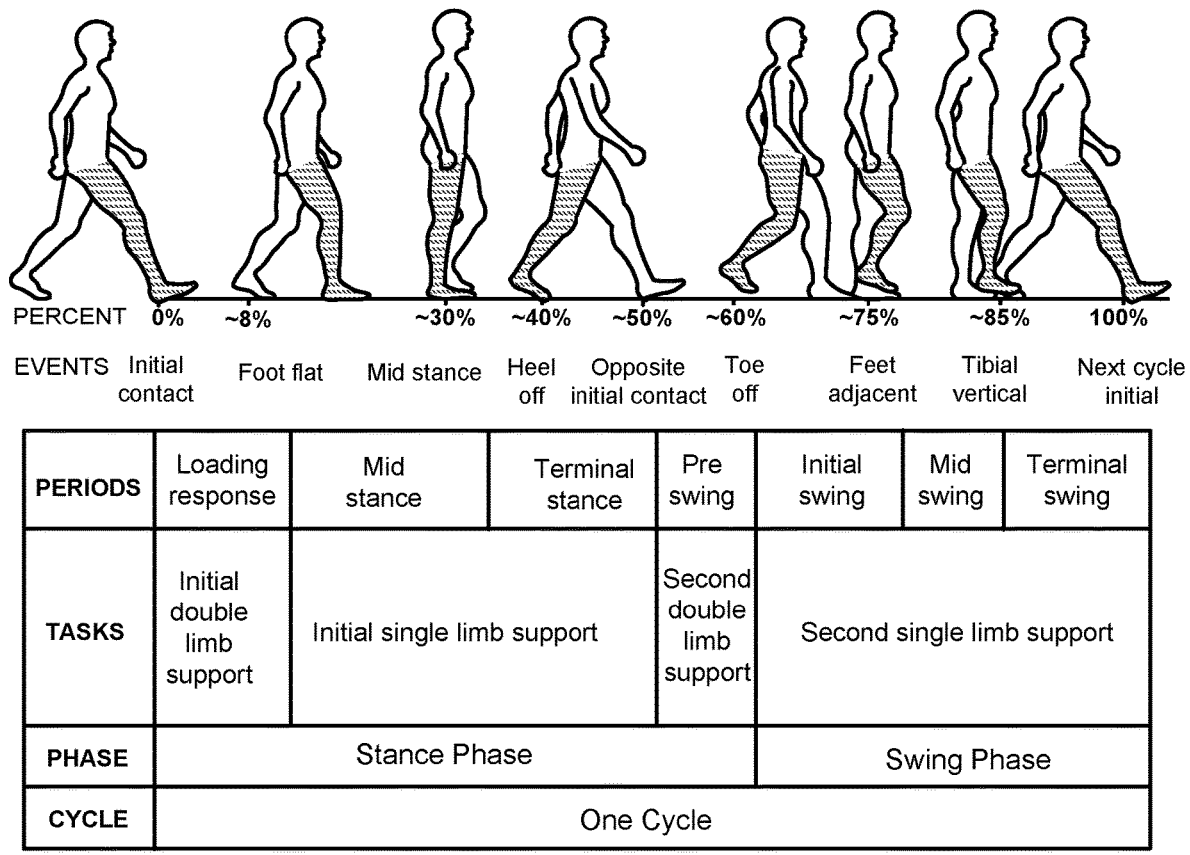
FIG. 4 illustrates one gait cycle of a right leg of a human subject.

FIG. 4 illustrates one gait cycle of a right leg of a human subject. Gait is the medical term used to describe human locomotion or the way humans walk. Studies have shown that every individual has a unique gait pattern. Such a gait pattern can be greatly affected (i.e., adversely affected) by injury or disease such as any number of upper motor neuron diseases, injuries, or disorders (e.g., stroke, multiple sclerosis, cerebral palsy, spinal cord injuries, traumatic brain injuries, etc.). In addition, a person's gait pattern can also be affected by the loss of muscle mass (e.g., due to aging, also known as sarcopenia) or injuries suffered as a result of broken bones from falls. Moreover, an athlete's gait pattern can also be adversely affected as a result of certain sports-related injuries such as anterior cruciate ligament (ACL) injuries, medial collateral ligament (MCL) injuries, posterior cruciate ligament (PCL) injuries, or a combination thereof.

The gait cycle is used to describe the motions from initial placement of the support heel on the ground to when the same heel contacts the ground the second time. A person's gait cycle can generally be broken down into a stance phase and a swing phase. The stance phase can further be broken down into the initial contact point, a loading response phase, a mid-stance phase, a terminal-stance phase, and a pre-swing phase. The swing phase can also further be broken down into the initial-swing phase, the mid-swing phase, and the terminal-swing phase.

The point of initial contact is the instantaneous point in time when the foot of the leading lower limb touches the ground. The loading response phase occupies about the first 10% (i.e., from 0% to about 10%) of the gait cycle and is the period when the foot comes in full contact with the floor and the body weight of the person is fully transferred on to the limb in question. The mid-stance phase occurs from about the 10% mark of the gait cycle to about the 30% mark of the gait cycle. This phase begins when the opposite (or contralateral) foot leaves the ground and continues as the body weight of the person shifts along the length of the foot until it is aligned over the forefoot. The terminal stance phase occurs from about the 30% mark of the gait cycle to about the 50% mark of the gait cycle. The terminal stance phase begins when the heel rises and ends when the opposite or contralateral foot contacts the ground. During this phase, the body weight of the person moves ahead of the forefoot. The pre-swing phase occurs when the gait cycle is at roughly 50% and ends when the gait cycle is at roughly 60% or 62%. The pre-swing phase begins when the opposite or contralateral foot contacts the ground and ends when the toe of the limb in question is off the ground. During this period, the stance limb is unloaded and the body weight of the person is shifted on to the opposite or contralateral limb. The initial-swing phase occurs from about the 60% mark of the gait cycle to about the 75% mark of the gait cycle. This phase occurs when the foot leaves the ground and continues until the swinging limb is directly under the body. The mid-swing phase occurs from about the 75% mark of the gait cycle to about the 85% mark of the gait cycle. During this phase, the swinging limb is further advanced and the tibia of the swinging leg is substantially vertical. Finally, the terminal-swing phase occupies the remaining 15% of the gait cycle (from about 85% to about 100%). During this phase, the tibia passes the point beyond perpendicular and the knee fully extends in preparation for the next heel contact.

When a person's gait is adversely affected due to disease or injury, the person can exhibit reduced walking speeds, reduced walking stability, and non-symmetrical walking. A person suffering trauma or the adverse effects of trauma or disease to the central nervous system can exhibit a condition known as drop foot. Those suffering from drop foot tend to drop their foot during the swing phase of the gait cycle and may compensate for this dragging by swinging their legs in a circular or exaggerated motion. This condition can lead to frequent falls and even short walks can be an exhaustive effort requiring excessive amounts of energy.

One treatment for drop foot or other gait cycle abnormalities can involve using electrical pulses to stimulate certain nerves and muscles of a person exhibiting signs of drop foot or other gait cycle abnormalities. In order to effectively stimulate the neuromuscular system of such a person, a treatment device must be capable of predicting or estimating the person's gait cycle percentage (or where they are in the gait cycle) to a certain degree of accuracy. Current treatment devices have been able to make such predictions or estimations using a heel sensor for sensing when heel strikes and heel lifts occur. However, such devices often require that the user wear footwear capable of housing the heel sensor and cannot use such devices when barefoot, wearing socks, or certain type of sandals. Moreover, such devices require the user to maintain and keep track of multiple sensor components, which complicates the use of such devices. Moreover, treatment devices designed to be used without a heel sensor may rely on a combination of accelerometers and gyroscopes for tilt measurement. These devices that rely on a tilt measurement for stimulation timing may have difficulties predicting the user's gait cycle percentage to a degree of accuracy needed to effectively stimulate the user's neuromuscular system. Tilt patterns may change frequently as a user's gait patterns change. Devices reliant on such tilt thresholds or measurements for stimulation timing require constant tuning to work optimally. This tuning procedure is often burdensome to users. For example, the device taught by U.S. Pat. No. 5,814,093 relies on tilt sensors. Such a device, when not tuned, can miss one out of every eight steps.

The FES device 100 disclosed herein overcomes such challenges by calculating a user's gait cycle percentage using real-time orientation and motion data obtained from the IMU 306 of the device 100. Real-time in this context can refer to use of orientation and motion data within milliseconds or seconds of their capture or collection. More specifically, the FES device 100 disclosed herein calculates a user's gait cycle percentage using real-time gyroscope readings obtained from the IMU 306 of the device 100.

Figure 7:
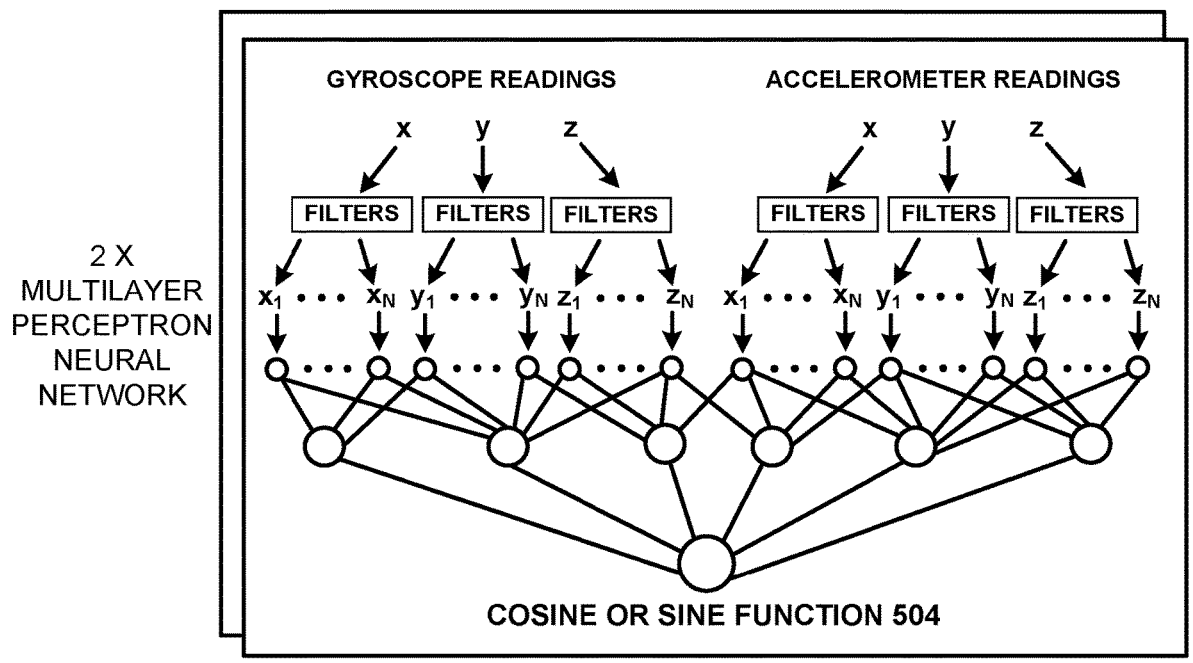
FIG. 7 illustrates an example machine learning algorithm used by the device to calculate a gait cycle percentage.

The one or more processors 302 of the FES device 100 can be programmed to execute instructions stored in the one or more memory units 304 of the device 100 to retrieve real-time gyroscope readings and accelerometer readings from the IMU 306 and calculate the gait cycle percentage by inputting the gyroscope readings and accelerometer readings into a machine learning algorithm 700 (see FIG. 7). The one or more processors 302 of the FES device 100 can also be programmed to execute instructions stored in the one or more memory units 304 of the device 100 to smooth out the gyroscope readings, the accelerometer readings, or a combination thereof with one or more low-pass filters prior to inputting the gyroscope readings and the accelerometer readings into the machine learning algorithm 700.

For example, the one or more processors 302 can be programmed to execute instructions stored in the one or more memory units 304 to retrieve gyroscope readings from the gyroscope 314 every ~20 milliseconds and calculate the gait cycle percentage by inputting such gyroscope readings into the machine learning algorithm 700. In one embodiment, the machine learning algorithm 700 is a feedforward neural network. For example, the machine learning algorithm 700 can be a multilayer perceptron neural network. In other embodiments, the machine learning algorithm 700 can be any machine learning algorithm capable of non-linear mapping.

The machine learning algorithm 700 can be trained or optimized by correlating IMU readings (e.g., gyroscope readings and/or accelerometer readings) with three-dimensional (3D) kinematic data obtained from computer vision. This can be done prior to usage of the FES device 100 during a training or data collection phase. The training or optimization of the machine learning algorithms 700 disclosed herein comprise method steps heretofore unseen by the applicant in the field of orthotics for gait modulation.

During the training or data collection phase, a model subject wearing the elastic wearable article having the IMU 306 coupled to the wearable article (or wearing only the IMU 306 at a location at or near a body location where the IMU 306 would be positioned if the elastic wearable article had been worn, e.g., on the anterior side of the lower leg below the knee) undertakes certain motions while having such motion be tracked by a plurality of cameras. For example, the model subject walks on a treadmill or walks a short distance while having the walking motion of the model subject tracked by a plurality of cameras surrounding (e.g., 360°) the model subject. The gyroscope readings of the gyroscope 314 within the IMU 306 (along with other data obtained from the IMU 306) can be collected during this motion capture step. Such IMU data (including the gyroscope readings) can then be correlated to 3D joint kinematic data obtained from the video images captured by the cameras.

In one embodiment, estimates of 3D joint kinematics can be obtained through "markerless" pose detection of video images of the walking motion of the model subject captured by the cameras. For example, Part Affinity Fields (PAFs) can be used to track the motion of the model subject in two-dimensions (2D) from video images captured by the cameras. Such 2D poses can then be triangulated to obtain 3D joint kinematic data. In other embodiments, the model subject can wear body markers and 3D joint kinematic data can be obtained from the tracking of such body markers. For example, 3D angles of major joints of the model subject can be obtained from the motion capture step. As a more specific example, 3D angles of the hip or upper thigh of the model subject (referred to herein as the "hip angle") relative to the medial line of the body of the subject can be obtained from the motion tracking step.

The hip angle can oscillate between about −50 degrees and +50 degrees as the model subject walks or runs (where −50 degrees and +50 degrees corresponds roughly to a maximally extended leg behind the subject or in front of the subject, respectively, and 0 degrees to a leg mid-stance or mid-swing). For example, as shown in FIG. 4, the hip angle can be between about +40 to about +50 degrees when a person makes initial contact (gait cycle percentage=0%) and can be between about −40 to about −50 degrees during the beginning of the terminal stance period when the leg extends behind the person (gait cycle percentage=about 40%). The hip angle can be back at about +40 to about +50 degrees at the end of the terminal swing stage when the person's heel is once again about to make contact with the ground (gait cycle percentage near 100%). As such, the hip angle of the model subject can serve as a useful proxy for the gait cycle percentage at this stage.

The hip angle can be represented using a periodic function such as a cosine function. A second periodic function, such as a sine function, can then be obtained by applying a Hilbert transform to the first periodic function (e.g., the cosine function). With the hip angle mapped to the two periodic functions, a machine learning algorithm 700 can be optimized to fit the IMU data (e.g., the gyroscope readings) obtained from the IMU 306 coupled to the leg of the model subject to the two periodic functions.

In one embodiment, the machine learning algorithm 700 can be a multilayer perceptron neural network. The multilayer perceptron neural network can be optimized to fit the IMU data (more specifically, the gyroscope readings from the gyroscope 314) to the two periodic functions. In this embodiment, the weights of the multilayer perceptron can be optimized to fit the IMU data (more specifically, the gyroscope readings from the gyroscope 314) to the two periodic functions. The weights of the multilayer perceptron can be fitted to the data by minimizing the error through one or more mathematical methods such as a stochastic gradient descent.

For example, a first multilayer perceptron neural network can be optimized to fit the IMU data (e.g., at least one of the gyroscope readings from the gyroscope 314 and the accelerometer readings from the accelerometer 316) to the cosine function and a second multilayer perceptron neural network can be optimized to fit the IMU data (more specifically, the gyroscope readings from the gyroscope 314) to the sine function.

Once the machine learning algorithm 700 is optimized and able to fit the IMU data to the two periodic functions derived from the motion tracking data, the optimized machine learning algorithm 700 can be used by the device 100 to calculate the gait cycle percentage directly from IMU data obtained from any user wearing the IMU 306 in roughly the same body location as the model subject (e.g., on the anterior side of the lower leg below the knee).

As a more specific example, once the weights of the two multilayer perceptron neural networks are optimized and able to fit the IMU data (e.g., the gyroscope readings and/or the accelerometer readings) to the two periodic functions derived from the motion tracking data, the two multilayer perceptron neural networks can be used by the device 100 to calculate the gait cycle percentage directly from IMU data (more specifically, gyroscope readings) obtained from any user wearing the IMU 306 in roughly the same body location as the model subject (e.g., on the anterior side of the lower leg below the knee).

One advantage of the methods and devices disclosed herein is that gait cycle percentages estimated or calculated using the methods disclosed herein (i.e., from IMU data collected by an IMU worn by the user) results in percentages with an accuracy rate of approximately 90% when compared to "actual" gait cycle percentages determined using motion-tracking techniques.

As will be discussed in more detail in the following sections, the EMS generator 310 of the device 100 can provide electrical stimulation to the nerves and muscles of the user via the electrodes 112 of the one or more electrode arrays 108 based in part on the gait cycle percentage calculated.

Figure 5:
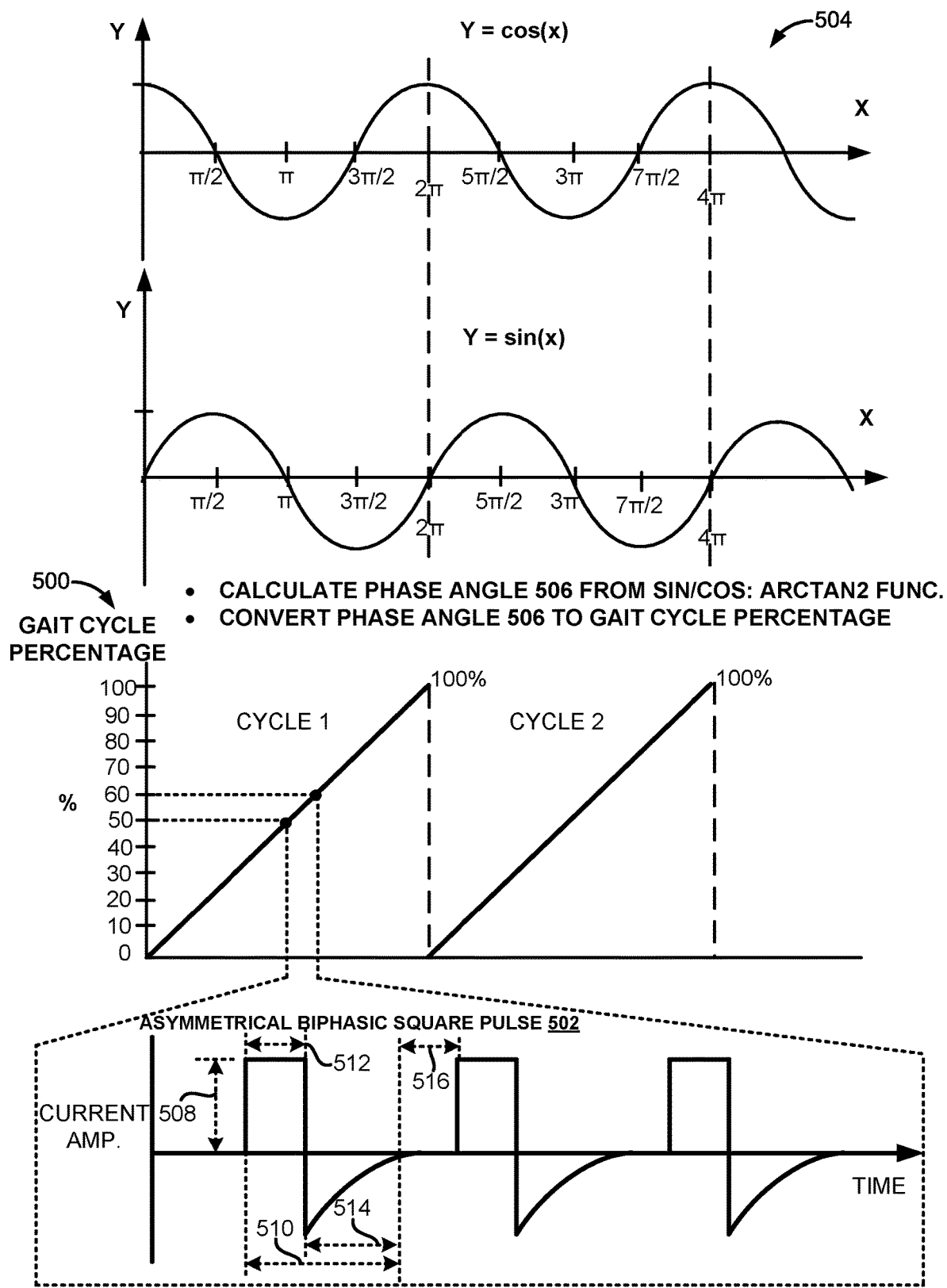
FIG. 5 illustrates example operations for calculating a gait cycle percentage and generating asymmetrical biphasic square pulses used to stimulate a neuromuscular system of a limb of a user.

FIG. 5 illustrates example operations for calculating a gait cycle percentage 500 and generating an asymmetrical biphasic square pulse 502 used to stimulate a neuromuscular system of a limb of a user. As previously discussed, a user can wear the FES device 100 by slipping on or donning the elastic wearable article (e.g., any of the first elastic sleeve 102, the second elastic sleeve 104, the cuff 122, or a combination thereof). The control unit 106 of the IMU 306 of the FES device 100 can be positioned on the anterior side of the lower leg of the user below the knee when the elastic wearable article is properly worn by the user. The user can then begin to walk while wearing the FES device 100.

The one or more processors 302 within the control unit 106 of the FES device 100 can be programmed to execute instructions stored in the one or more memory units 304 to retrieve gyroscope readings from the gyroscope 314 of the IMU 306. The instructions can dictate that gyroscope readings and/or accelerometer readings be retrieved every ~20 milliseconds (or between about 10 milliseconds and 40 milliseconds). The gyroscope readings and/or accelerometer readings can then be provided as inputs into the optimized machine learning algorithm 700 (e.g., a feedforward neural network such as a multilayer perceptron neural network).

The one or more processors 302 can then be programmed to execute further instructions to map the gyroscope readings and/or the accelerometer readings to two periodic functions 504. In one embodiment, the one or more processors 302 can then be programmed to execute further instructions to map the gyroscope readings and/or the accelerometer readings to both a cosine function and a sine function. As previously discussed, the machine learning algorithm 700 can be a multilayer perceptron neural network. The one or more processors 302 can be programmed to execute instructions to use the two optimized multilayer perceptron neural networks to map the gyroscope readings to a cosine function and a sine function (one optimized multilayer perceptron neural network for each periodic function 504). It is important that the IMU data (e.g., the gyroscope readings) be mapped to both the cosine and sine functions as the nature of such functions (since, for example, $\sin(0)=0$ and $\sin(\pi)=0$) would not allow the phase angle (and eventually, the gait cycle percentage) to be obtained from only one such function.

The one or more processors 302 can also be programmed to execute additional instructions to smooth out the two periodic functions 504 using one or more low-pass filter functions. For example, the low-pass filter functions can be set to discard all frequencies higher than about 10 Hz and allow all frequencies between about 1 Hz and 10 Hz to pass through. As a more specific example, the low-pass filter function used can be represented by the following relationship where y(n) is the output and x(n) is the input:

$$y(n)=x(n)*0.15+y(n-1)*0.85$$

Besides the relationship presented above, other low-pass filter functions can also be optimized or configured to smooth out the periodic functions. Once the periodic functions are smoothed out, the one or more processors 302 can be programmed to execute instructions to calculate a phase angle 506 between the two periodic functions. In one embodiment, calculating the phase angle 506 can be done using the arctan 2 (also known as atan 2) function. For example, the phase angle 506 can be calculated using the following relationship:

$$\text{phase angle}=\arctan 2(\sin(x),\cos(x))$$

Having determined the phase angle, the one or more processors 302 can be programmed to execute further instructions to convert the phase angle to a gait cycle percentage 500. In one embodiment, the gait cycle percentage 500 can be calculated from the phase angle using the following relationship:

$$\text{gait cycle percentage}=(\text{phase angle}+\pi)*(100/(2*\pi))$$

One discovery made by the applicant is that calculating the gait cycle percentage using the methods described herein results in a more accurate gait cycle percentage than directly trying to map the IMU data to the gait cycle percentage. For example, as shown in FIGS. 4 and 5, the user's leg is in the same position when the gait cycle percentage is at 0% and 100% for each cycle. As such, mapping similar IMU data directly to such widely differing gait cycle percentage values is problematic. The solution provided by the applicant is to map the IMU data to two separate periodic functions and to use the phase angle calculated between the two periodic functions to determine the gait cycle percentage.

Once the device 100 has calculated/estimated the gait cycle percentage 500, the one or more processors 302 can instruct the EMS generator 310 to provide electrical stimulation to the nerves and muscles of the limb in physical contact with the electrodes 112 of the one or more electrode arrays 108. In this manner, the electrical stimulation can be timed and set by the gait cycle percentages 500 calculated.

As shown in FIG. 5, the one or more processors 302 can be programmed to execute instructions stored in the one or more memory units 304 to instruct the EMS generator 310 to generate a plurality of asymmetrical biphasic square pulses 502 for transmission to electrodes 112 of the one or more electrode arrays 108. The pulses can provide electrical stimulation to certain nerves and muscles of the user in physical contact with the electrodes 112. For example, the EMS generator 310 can be instructed to generate a plurality of asymmetrical biphasic square pulses 502 at a first gait cycle percentage (e.g., a gait cycle percentage of 50%) and terminate the pulses at a second gait cycle percentage (e.g., a gait cycle percentage of 60%).

During this entire process, the one or more processors 302 can also instruct the wireless communication module 308 to continuously or periodically transmit readings from the IMU 306 (e.g., gyroscope readings, accelerometer readings, magnetometer readings, etc.) to at least one of a client device 100 (e.g., a smartphone carried by the user) and a server 334 via one or more networks 332. Moreover, the one or more processors 302 can also instruct the wireless communication module 308 to continuously or periodically transmit the gait cycle percentages 500 calculated to at least one of a client device 100 and a server 334 via one or more networks 332. The readings from the IMU 306 (e.g., gyroscope readings, accelerometer readings, magnetometer readings, etc.), the gait cycle percentages 500 calculated, and any other data or information collected by the FES device 100 can also be stored in one or more databases 336 accessible to the device 100, the client device 100, or the server 334 via one or more networks 332.

The one or more processors 302 can also use machine learning to classify raw inertial measurements to human activities that may require altering stimulation control. These human activities can include locomotor patterns such as sitting, standing, walking, jogging, running, stair ascent, stair descent, cycling, rowing, jumping, tripping, scuffing, etc. Numerous methods for an activity classifier can be employed simultaneously. Such classifiers can include supervised and unsupervised classifiers or classification techniques for classifying human activities. Examples of supervised classification techniques include k-Nearest Neighbor (k-NN), Support Vector Machine (SVM), Gaussian Mixture Models (GMM), and Random Forest (RF). Unsupervised classification techniques can include k-Means, GMM, and Hidden Markov Models (HMM). The classifier can predict the activity undertaken by the user and can be used to determine the controller hierarchical finite state machine, whereby each state can employ a unique control algorithm for electrical stimulation.

A multi-nodal network of wearable devices (for example, bilateral FES devices 100 worn below the knee, additional strap or cuff-type devices worn around the thigh, foot worn sensors, etc.) can further inform the activity classifier or the gait cycle percentage calculations. Additional nodes or devices can improve kinematic modeling and provide additional inputs to the machine-learning algorithm (e.g., neural network) and can result in increased fidelity (or enhanced performance) of the algorithms.

In some embodiments, a high-bandwidth wireless communication protocol, such as the Zigbee™ IEEE 802.15.4 protocol, can be used to allow the multi-nodal network of wearable devices to communication with one another.

FIG. 5 illustrates that the asymmetrical biphasic square pulses 502 can comprise a max amplitude 508, a pulse duration 510, a first phase duration 512, a second phase duration 514, and an interpulse interval duration 516. As previously discussed, the user can calibrate or set the stimulation strength by customizing the pulse parameters. In some embodiments, the user can calibrate or set the stimulation strength by customizing any of the max amplitude 508, the pulse duration 510, the first phase duration 512, the second phase duration 514, and the interpulse interval duration 516. Moreover, the user can also customize the frequency of the pulses 502. For example, the user can set the max amplitude 508 between about 20 mA and about 80 mA. In addition, the user can also set the pulse duration 510 between about 50 µs to about 300 µs. Moreover, the user can set the interpulse interval duration 516 between about 10 µs to about 50 µs. Furthermore, the user can set the frequency between about 30 Hz and 40 Hz. The user can customize the pulse parameters (and, thereby, the stimulation strength) based on personal preference, comfort, or at the direction/suggestion of a physical therapist, physician, or other medical professional. As previously discussed, the user can also customize the location of the stimulation by selecting which pair(s) of electrodes 112 are stimulated.

As shown in FIG. 5, being able to accurately estimate or calculate the gait cycle percentage 500 is important as the timing of the electrical stimulation (i.e., the generation and termination of the asymmetrical biphasic square pulses 502) is determined largely on the gait cycle percentages 500 calculated. Moreover, since each individual's gait pattern is different and a person's gait pattern can change based on the walking surface, the time of day, and overall environment, being able to accurately calculate an individual's gait cycle percentage based on real-time IMU data is crucial in order to effectively modulate the gait of such an individual.

Figure 6:
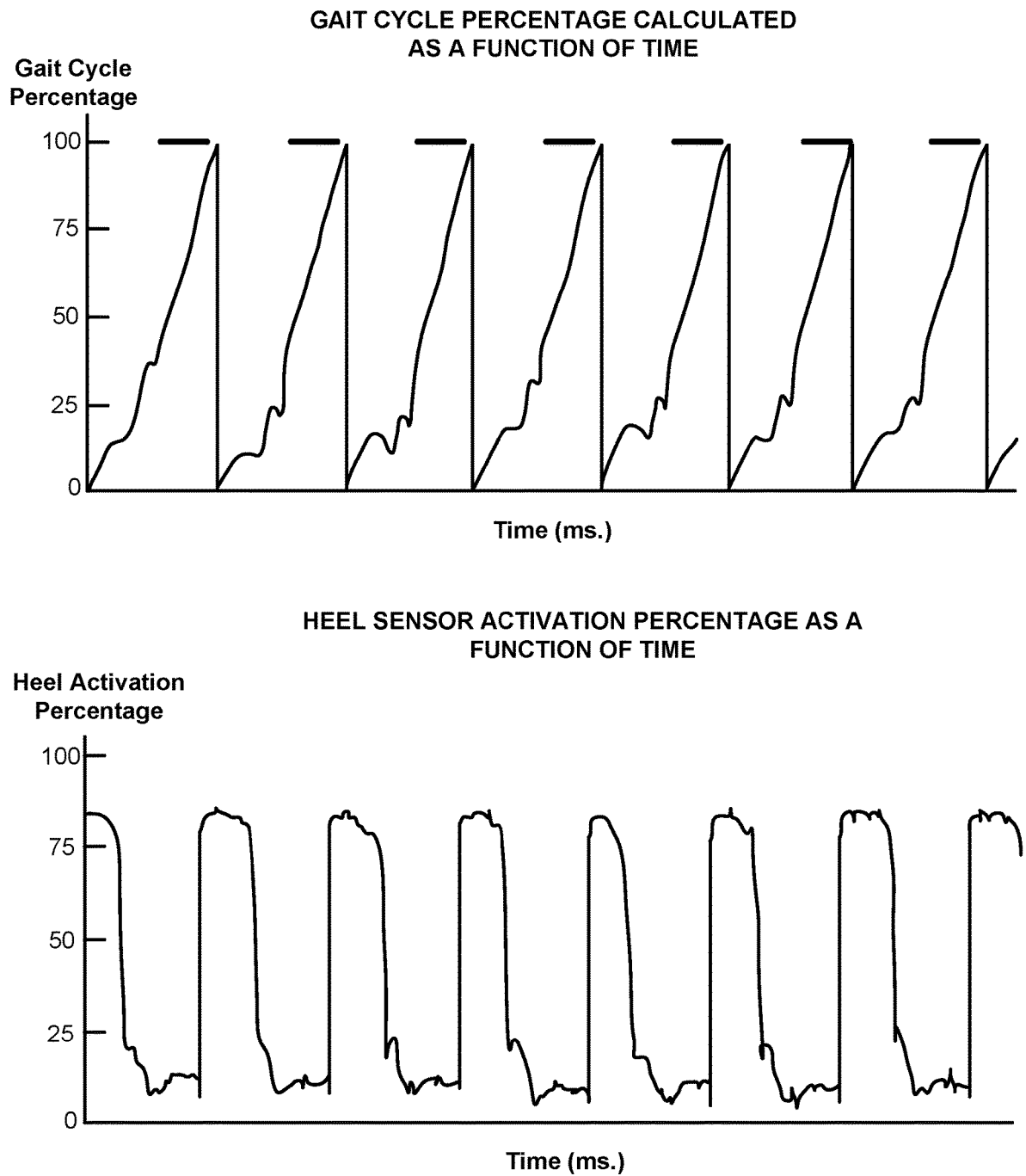
FIG. 6 are graphs comparing gait cycle percentages calculated to heel sensor data collected as a function of time.

FIG. 6 illustrates graphs comparing calculated gait cycle percentages to heel sensor data as a function of time. The heel sensor data can be collected from a force sensing resistor placed under the heel of a user. The graphs show that stimulation timing based on the gait cycle percentages calculated using the methods disclosed herein was consistent and more reliable than devices that used tilt thresholds or tilt measurements to coordinate stimulation.

FIG. 7 illustrates an example machine learning algorithm 700 used by the device to calculate the gait cycle percentage 500. FIG. 7 also illustrates that the gyroscope readings and the accelerometer readings can be filtered with a set of at least three filters before being mapped to phase through the neural network. For example, the filters can be low-pass filters with cutoffs of 4 Hz, 1 Hz, and 0.25 Hz. In principle, the filtering can be accomplished using any number of low-pass filters spaced far enough apart. For example, this could be a total of $(3+3)*3=18$ values which can be used as inputs to the machine learning algorithm 700 to predict the phase.

In some embodiments, the machine learning algorithm 700 can be any machine learning algorithm configured to handle non-linear mapping. In one embodiment, the machine learning algorithm 700 is a feedforward artificial neural network such as a multilayer perceptron neural network. In other embodiments, the machine learning algorithm 700 can be a random forest algorithm, a support vector machine (SVM) algorithm, or a combination thereof.

When the machine learning algorithm 700 is a multilayer perceptron neural network, the network can be set up as multiple "layers" of matrix multiplication functions followed by the application of a nonlinear function. In one specific embodiment, the rectifier $f(x)=\max(0, x)$ can be used as the nonlinear function. Given an input x, the multilayer perceptron with weights corresponding to matrix A for the first layer and matrix B for the second layer can have the output $y=f(B(f(A(x))))$ where $f(x)=\max(0, x)$. The weights of the multilayer perceptron neural network can be fitted from one dataset to another by minimizing the error through stochastic gradient descent.

One advantage of the devices and methods disclosed herein is that the machine learning algorithm 700 selected by the applicant is robust enough to handle the mapping tasks yet also fast enough to be run in real-time using the processors 302 of the control unit 106 (e.g., a processor operating at a clock frequency of at least 12 MHz).

A number of embodiments have been described. Nevertheless, it will be understood by one of ordinary skill in the art that various modifications may be made without departing from the spirit and scope of the embodiments. In addition, the flowcharts or logic flows depicted in the figures do not require the particular order shown, or sequential order, to achieve desirable results. In addition, other steps or operations may be provided, or steps or operations may be eliminated, from the described flows, and other components may be added to, or removed from, the described systems. Accordingly, other embodiments are within the scope of the following claims.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, and patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

It will be understood by one of ordinary skill in the art that the various methods disclosed herein may be embodied in a non-transitory readable medium, machine-readable medium, and/or a machine accessible medium comprising instructions compatible, readable, and/or executable by a processor or server processor of a machine, device, or computing device. The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

We claim:

1. A functional electrical stimulation (FES) device, comprising:
    one or more elastic wearable articles configured to be worn on a limb of a user;
    a control unit comprising a wireless communication module, one or more processors, one or more memory units, a portable power supply, an electrical muscle stimulation (EMS) generator, and an inertial measurement unit (IMU), wherein a housing of the control unit is coupled to at least one of the one or more elastic wearable articles, wherein the IMU comprises at least a gyroscope and an accelerometer;
    one or more electrode arrays configured to be in electrical communication with the EMS generator, wherein at least part of each of the one or more electrode arrays is configured to be in physical contact with the limb of the user,
    wherein the one or more processors are programmed to execute instructions stored in the one or more memory units to:
        retrieve gyroscope readings from the IMU,
        retrieve accelerometer readings from the IMU,
        calculate a gait cycle percentage by inputting at least the gyroscope readings into a machine learning algorithm,
        map the gyroscope readings and the accelerometer readings to three-dimensional angles of at least one of a hip, a knee, and a foot of the user throughout a gait cycle,
        determine at least one of a foot strike pattern, a foot inclination angle at initial contact, a tibia angle at loading response, a hip extension during late stance, a trunk lean, a heel eversion, a foot progression angle, a pelvic drop, a knee flexion during stance, a stride length, a knee window, a vertical displacement of the center mass, and a heel whip of the user based in part on the gait cycle percentage calculated, the gyroscope readings, the accelerometer readings, and the mapped three-dimensional angles, and
        instruct the EMS generator to provide electrical stimulation to nerves and muscles of the limb via the one or more electrode arrays based in part on the gait cycle percentage calculated.

2. The device of claim 1, wherein the one or more elastic wearable articles comprises a first elastic article and a second elastic article, wherein the first elastic article is configured to be worn on a thigh of the user and the second elastic article is configured to be worn on a lower leg of the user between a knee and an ankle of the user.

3. The device of claim 2, wherein the one or more electrode arrays comprises at least a first upper leg array, a second upper leg array, a first lower leg array, and a second lower leg array, wherein the first upper leg array and the second upper leg array and wherein the first upper leg array and the second upper leg array are configured to be in physical contact with a skin surface in proximity to a hamstring or quadricep of the user, and wherein the first lower leg array and the second lower leg array are configured to be in physical contact with the skin surface in proximity to a tibialis anterior of the user.

4. The device of claim 1, wherein the elastic wearable article is an elastic cuff configured to be worn on a lower leg of the user between a knee and an ankle of the user, wherein the one or more electrode arrays comprises an upper leg array and a lower leg array, wherein the upper leg array is configured to be in physical contact with a skin surface in proximity to a hamstring or quadricep of the user, and wherein the lower leg array is configured to be in physical contact with the skin surface in proximity to a tibialis anterior of the user.

5. The device of claim 1, wherein the machine learning algorithm comprises one or more multilayer perceptron neural networks.

6. The device of claim 1, wherein the wireless communication module is configured to wirelessly transmit walking metrics calculated from the IMU and the gait cycle percentage to at least one of a client device of the user and a database accessible via a communication network.

7. The device of claim 1, wherein the one or more processors are programmed to execute additional instructions stored in the one or more memory units to instruct the EMS generator to generate a plurality of asymmetrical biphasic square pulses for transmission to electrodes of the one or more electrode arrays to provide the electrical stimulation to the nerves and muscles of the limb of the user.

8. A functional electrical stimulation (FES) device, comprising:
one or more elastic wearable articles configured to be worn on a limb of a user;
a control unit comprising a wireless communication module, one or more processors, one or more memory units, a portable power supply, an electrical muscle stimulation (EMS) generator, and an inertial measurement unit (IMU), wherein a housing of the control unit is coupled to at least one of the one or more elastic wearable articles, wherein the IMU comprises at least a gyroscope;
one or more electrode arrays configured to be in electrical communication with the EMS generator, wherein at least part of each of the one or more electrode arrays is configured to be in physical contact with the limb of the user,
wherein the one or more processors are programmed to execute instructions stored in the one or more memory units to:
retrieve gyroscope readings from the IMU,
calculate a gait cycle percentage by inputting at least the gyroscope readings into a machine learning algorithm,
map the gyroscope readings to two periodic functions using the machine learning algorithm,
calculate a phase angle from the two periodic functions,
convert the phase angle to the gait cycle percentage, and
instruct the EMS generator to provide electrical stimulation to nerves and muscles of the limb via the one or more electrode arrays based in part on the gait cycle percentage calculated.

9. The device of claim 8, wherein the one or more processors are programmed to execute instructions stored in the one or more memory units to smooth out the two periodic functions using one or more low-pass filter functions prior to calculating the phase angle.

10. A method of modulating a movement of a limb of a user, comprising:
retrieving, using one or more processors, gyroscope readings from a gyroscope and accelerometer readings from an accelerometer of an inertial measurement unit (IMU), wherein the one or more processors and the IMU are part of a control unit further comprising a wireless communication module, one or more memory units, a portable power supply, and an electrical muscle stimulation (EMS) generator, and wherein a housing of the control unit is coupled to at least one of one or more elastic wearable articles configured to be worn on the limb of the user;
calculating, using the one or more processors, a gait cycle percentage by inputting at least the gyroscope readings into a machine learning algorithm;
mapping the gyroscope readings and the accelerometer readings to three-dimensional angles of at least one of a hip, a knee, and a foot of the user throughout a gait cycle;
determining at least one of a foot strike pattern, a foot inclination angle at initial contact, a tibia angle at loading response, a hip extension during late stance, a trunk lean, a heel eversion, a foot progression angle, a pelvic drop, a knee flexion during stance, a stride length, a knee window, a vertical displacement of the center mass, and a heel whip of the user based in part on the gait cycle percentage calculated, the gyroscope readings, the accelerometer readings, and the mapped three-dimensional angles; and
instructing the EMS generator to provide electrical stimulation to nerves and muscles of the limb of the user via one or more electrode arrays based in part on the gait cycle percentage calculated, wherein the one or more electrode arrays are in electrical communication with the control unit and at least part of each of the one or more electrode arrays are configured to be in physical contact with the limb of the user.

11. The method of claim 10, wherein the one or more elastic wearable articles comprises a first elastic article and a second elastic article, wherein the first elastic article is configured to be worn on a thigh of the user and the second elastic article is configured to be worn on a lower leg of the user between a knee and an ankle of the user.

12. The method of claim 11, wherein the one or more electrode arrays comprises at least a first upper leg array, a second upper leg array, a first lower leg array, and a second lower leg array, wherein the first upper leg array and the second upper leg array are configured to be in physical contact with a skin surface in proximity to a hamstring or quadricep of the user, and wherein the first lower leg array and the second lower leg array are configured to be in physical contact with the skin surface in proximity to a tibialis anterior of the user.

13. The method of claim 10, wherein the elastic wearable article is an elastic cuff configured to be worn on a lower leg of the user between a knee and an ankle of the user, wherein the one or more electrode arrays comprises an upper leg array and a lower leg array, wherein the upper leg array is configured to be in physical contact with a skin surface in proximity to a hamstring or quadricep of the user, and wherein the lower leg array is configured to be in physical contact with the skin surface in proximity to a tibialis anterior of the user.

14. The method of claim 10, wherein the machine learning algorithm comprises one or more multilayer perceptron neural networks.

15. The method of claim 10, further comprising transmitting, using the wireless communication module, walking metrics calculated from the IMU and the gait cycle percentage to at least one of a client device of the user and a database accessible via a communication network.

16. The method of claim 10, further comprising instructing the EMS generator to generate a plurality of asymmetrical biphasic square pulses for transmission to electrodes of the one or more electrode arrays to provide the electrical stimulation to the nerves and muscles of the limb of the user.

17. The method of claim 10, further comprising smoothing out, using the one or more processors, at least one of the gyroscope readings and accelerometer readings with one or more low-pass filters prior to inputting the gyroscope readings and the accelerometer readings into the machine learning algorithm.

18. A method of modulating a movement of a limb of a user, comprising:
retrieving, using one or more processors, gyroscope readings from a gyroscope of an inertial measurement unit (IMU), wherein the one or more processors and the IMU are part of a control unit further comprising a wireless communication module, one or more memory units, a portable power supply, and an electrical muscle stimulation (EMS) generator, and wherein a housing of the control unit is coupled to at least one of one or more elastic wearable articles configured to be worn on the limb of the user;
calculating, using the one or more processors, a gait cycle percentage by inputting at least the gyroscope readings into a machine learning algorithm;
mapping, using the one or more processors, the gyroscope measurements to two periodic functions using the machine learning algorithm;
calculating a phase angle from the two periodic functions;
converting the phase angle to the gait cycle percentage; and
instructing the EMS generator to provide electrical stimulation to nerves and muscles of the limb of the user via one or more electrode arrays based in part on the gait cycle percentage calculated, wherein the one or more electrode arrays are in electrical communication with the control unit and at least part of each of the one or more electrode arrays are configured to be in physical contact with the limb of the user.

19. The method of claim 18, further comprising smoothing out, using the one or more processors, the two periodic functions using one or more low-pass filter functions prior to calculating the phase angle.

* * * * *